(12) United States Patent
Burk et al.

(10) Patent No.: US 6,359,181 B1
(45) Date of Patent: *Mar. 19, 2002

(54) CYCLOPENTANE 1-HYDROXY ALKYL OR ALKENYL-2-ONE OR 2-HYDROXY DERIVATIVES AS THERAPEUTIC AGENTS

(75) Inventors: Robert M. Burk, Laguna Beach; Mark Holoboski; Mari F. Posner, both of Laguna Niguel, all of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/915,908

(22) Filed: Jul. 26, 2001

Related U.S. Application Data

(63) Continuation of application No. 09/850,834, filed on May 8, 2001, which is a continuation of application No. 09/665,791, filed on Sep. 20, 2000, now Pat. No. 6,248,783.

(51) Int. Cl.$^7$ .................................... C07C 455/00
(52) U.S. Cl. .................. 568/838; 560/231; 568/379
(58) Field of Search ........................... 568/838

(56) References Cited

U.S. PATENT DOCUMENTS

| 4,994,274 A | 2/1991 | Chan et al. |
| 5,028,624 A | 7/1991 | Chan et al. |
| 5,034,413 A | 7/1991 | Chan et al. |
| 5,446,041 A | 8/1995 | Chan et al. |

OTHER PUBLICATIONS

Bito, L.Z., *Biological Protection with Prostaglandins*, "Prostaglandins and Related Compounds as Potential Ocular Therapeutic Agents", vol. 1, Chapter 18, 1985, pp. 231–252.
Bito, L.Z., *Glaucoma, Applied Pharmacology in the Medical Treatment*, "Prostaglandins, Other Eicosanoids, and Their Derivatives as Potential Antiglaucoma Agents",1984, Chapter 20, pp. 477–505.

Nilsson et al, Invest. Ophthalmol. Vis. Sci. (suppl), 284 (1987), Arvo Abstracts 9–6:00.
Bito, L.Z., Arch. Ophthalmol. "Prostaglandins" "Old Concepts and New Perspectives", vol. 105, pp. 1036–1039 (1987).
Siebold et al, Prodrug 5 3, "Esterified protaglandin shows 'potent' promise",1989.
Simon, Z, 1982, Timisoara Md., 27(1), 15–18.

*Primary Examiner*—Robert Gerstl
(74) *Attorney, Agent, or Firm*—Robert J. Baran; Martin A. Voet; Carlos A. Fisher

(57) ABSTRACT

The present invention provides a novel compound represented by the general formula I;

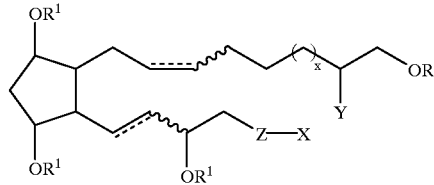

wherein R is H or COR$^3$;
R$^1$ is H, R$^2$, phenyl, or COR$^3$, wherein R$^2$ is C$_1$–C$_5$ lower alkyl and R$^3$ is R$^2$ or phenyl;
Z is CH$_2$ or O;
Y is OH, OCOR$^3$ or =O;
x is 0 or 1; and
X is C$_1$–C$_5$ n-alkyl, C$_3$–C$_7$ cycloalkyl, phenyl, furanyl, thienyl or substituted derivatives thereof, wherein the substituents maybe selected from the group consisting of C$_1$–C$_5$ alkyl, halogen, CF$_3$, CN, NO$_2$, NR$^4{}_2$, CO$_2$R$^4$ and OR$^4$ wherein
R$^4$ is hydrogen or C$_1$–C$_5$ alkyl and dotted lines represent the presence or absence of a double bond and wavy lines represent a cis or trans bond. These novel compounds are especially useful for treating elevated intraocular pressure (ocular hypertension) and glaucoma.

8 Claims, 9 Drawing Sheets

CYCLOPENTANE 1-HYDROXY ALKYL OR ALKENYL-2-ONE OR 2-HYDROXY DERIVATIVES AS THERAPEUTIC AGENTS

CROSS REFERENCE TO RELATED APPLICATION

This application is a continuation of and claims the benefit of U.S. patent application Ser. No. 09/850,834 filed May 8, 2001, which is a continuation of U.S. patent application Ser. No. 09/665,791 filed Sep. 20, 2000, now U.S. Pat. No. 6,248,783.

BACKGROUND OF THE INVENTION

1. Field of the Invention

The present invention relates to cyclopentane 1-hydroxy alkyl or alkenyl-2-one or 2-hydroxy derivatives as therapeutic agents. These compounds are potent ocular hypotensives and are particularly suited for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

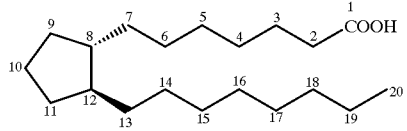

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et.al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed Oct. 10, 1990), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175,476 (filed Dec. 29, 1993). Similarly, 11,15- 9,15 and 9,11-diesters of prostaglandins, for example 11,15-dipivaloyl $PGF_{2\alpha}$ are known to have ocular hypotensive activity. See the co-pending patent applications U.S. Ser. No. 385,645 (filed Jul. 07, 1989, now U.S. Pat. No. 4,994,274), U.S. Ser. No. 584,370 (filed Sep. 18, 1990, now U.S. Pat. No. 5,028,624) and U.S. Ser. No. 585,284 (filed Sep. 18, 1990, now U.S. Pat. No. 5,034,413). The disclosures of all of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I

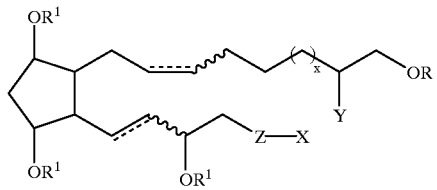

wherein R is H or $COR^3$;
  $R^1$ is H, $R^2$, phenyl, or $COR^3$, wherein $R^2$ is $C_1$–$C_5$ lower alkyl and $R^3$ is $R^2$ or phenyl;
  Z is $CH_2$ or O;
  Y is OH, $OCOR^3$ or =O;
  x is 0 or 1; and
  X is $C_1$–$C_5$ n-alkyl, $C_3$–$C_7$ cycloalkyl, phenyl, furanyl, thienyl or substituted derivatives thereof, wherein the substituents maybe selected from the group consisting of $C_1$–$C_5$ alkyl, halogen, $CF_3$, CN, $NO_2$, $NR^4_2$, $CO_2R^4$ and $OR^4$ wherein
    $R^4$ is hydrogen or $C_1$–$C_5$ alkyl and dotted lines represent the presence or absence of a double bond and wavy lines represent a cis or trans bond.

In a still further aspect, the present invention relates to a pharmaceutical product, comprising
  a container adapted to dispense its contents in a metered form; and
  an ophthalmic solution therein, as hereinabove defined.

Finally, certain of the compounds represented by the above formula, disclosed below and utilized in the method of the present invention are novel and unobvious.

BRIEF DESCRIPTION OF THE DRAWING FIGURES

DETAILED DESCRIPTION OF THE INVENTION

Figure 1:
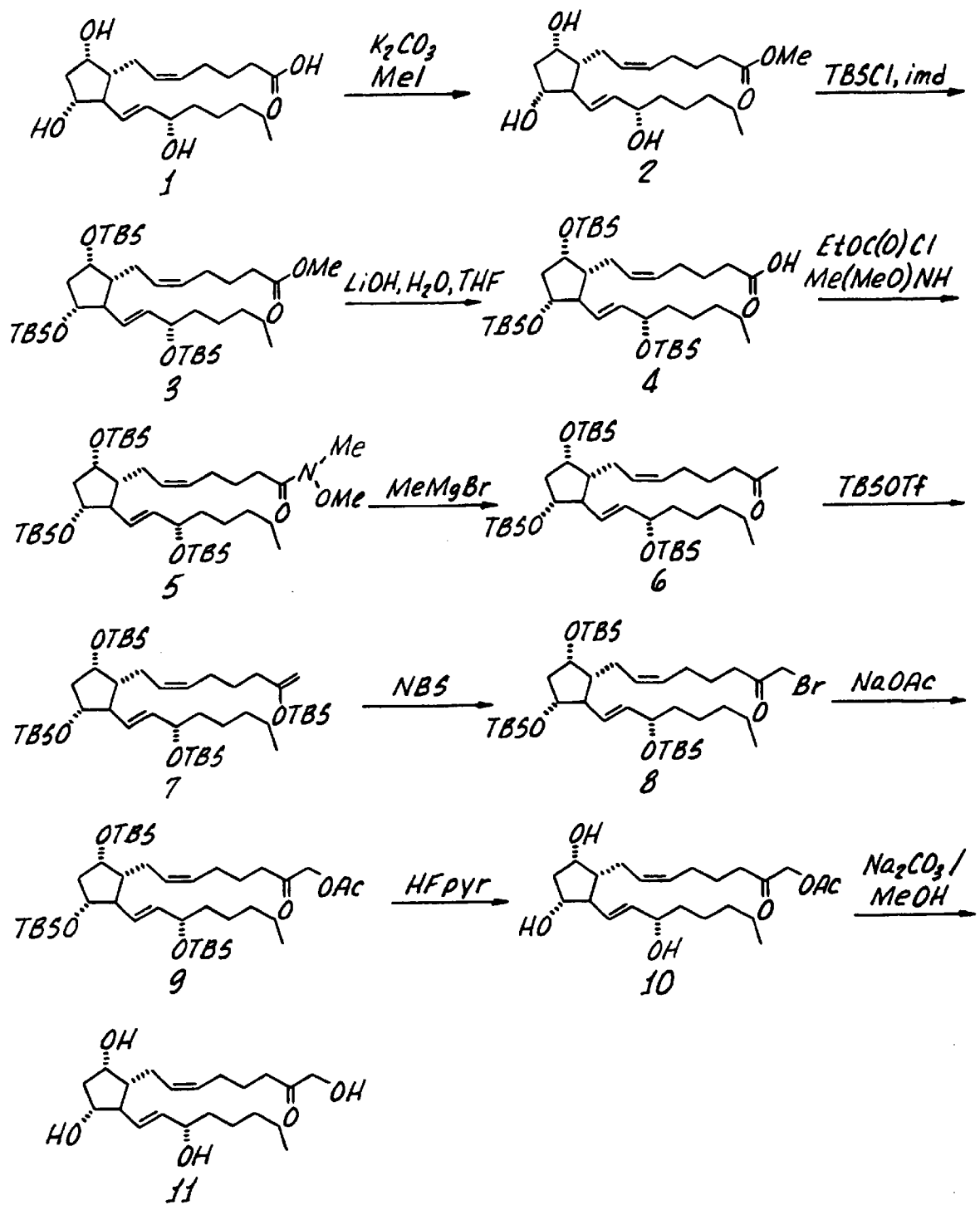
FIG. 1 is a schematic of the chemical synthesis of certain compounds of the present invention, in particular the compound of Example 11, below.
Figure 2A:
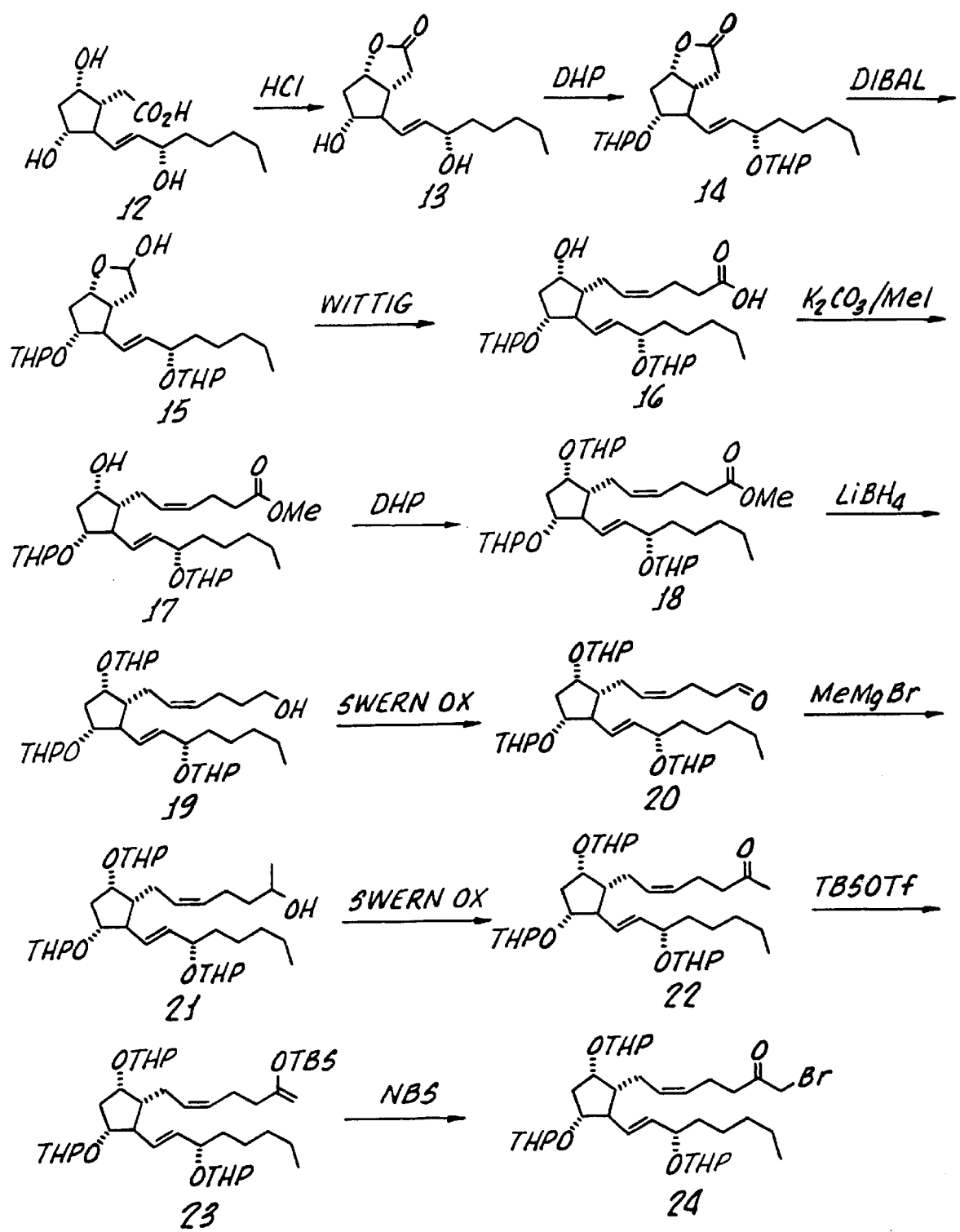
FIG. 2 is a schematic of the chemical synthesis of certain compounds of the present invention, in particular the compounds of Examples 26 and 27, below.
Figure 2B:
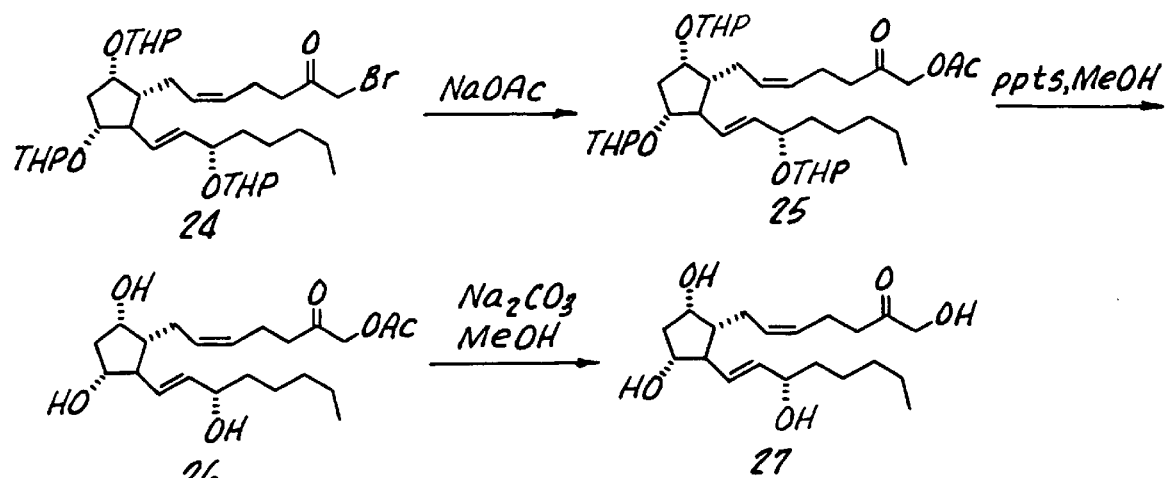
Figure 3A:
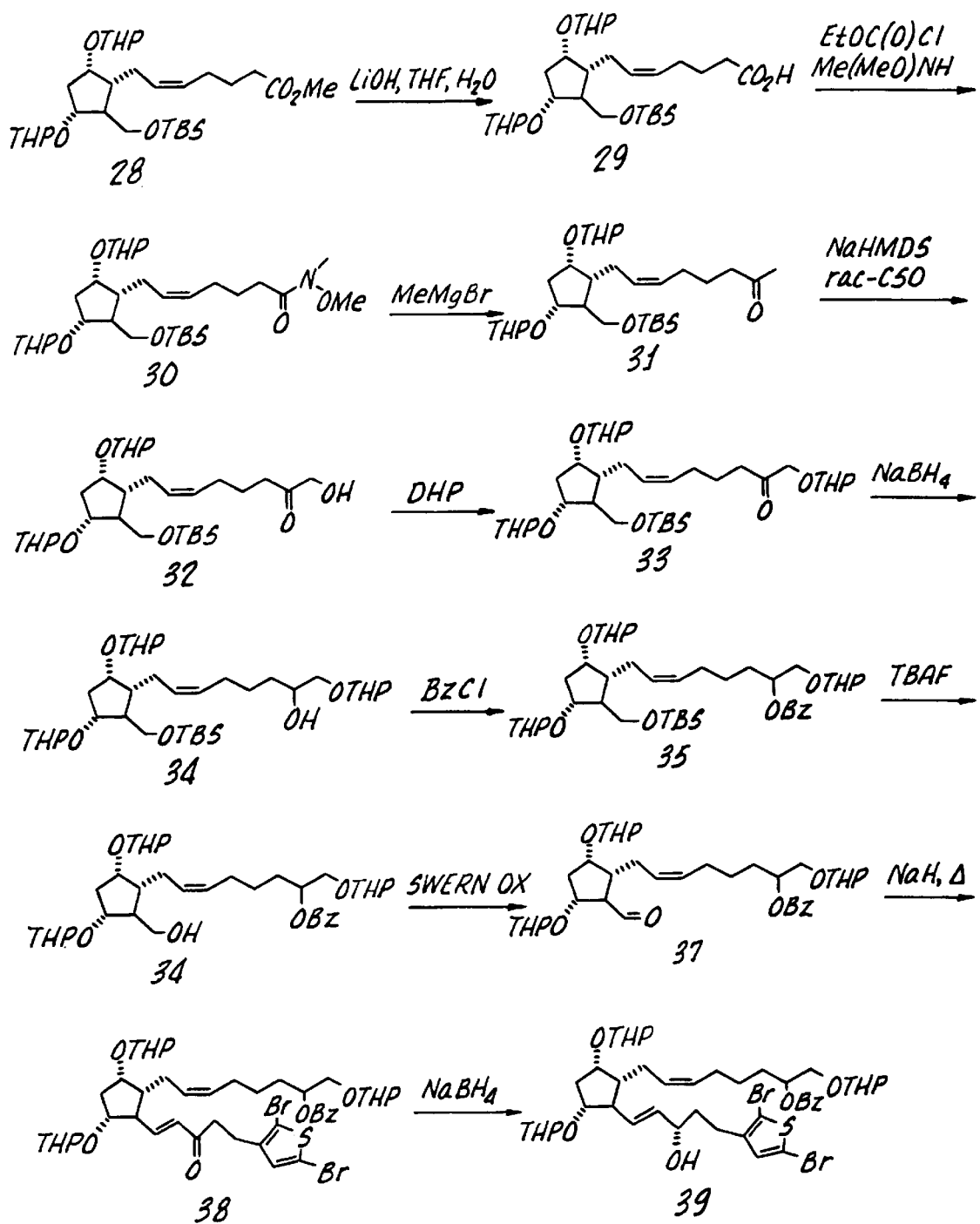
FIG. 3 is a schematic of the chemical synthesis of certain compounds of the present invention, in particular the compound of Example 43, below.
Figure 3B:
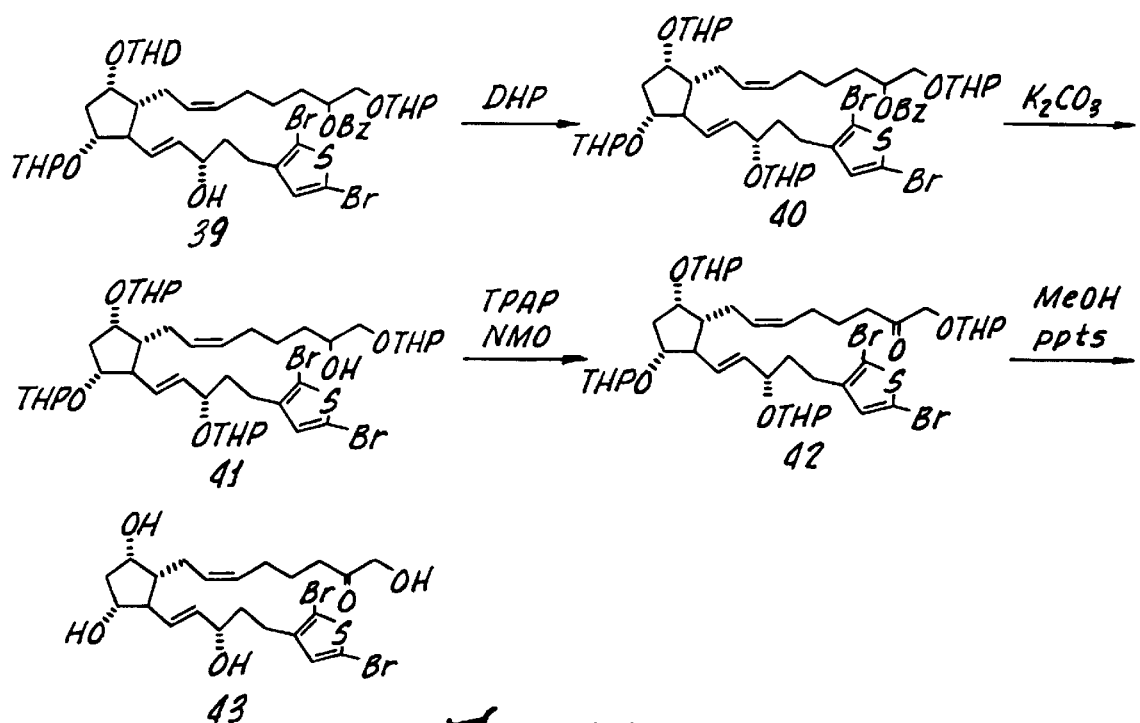
Figure 4:
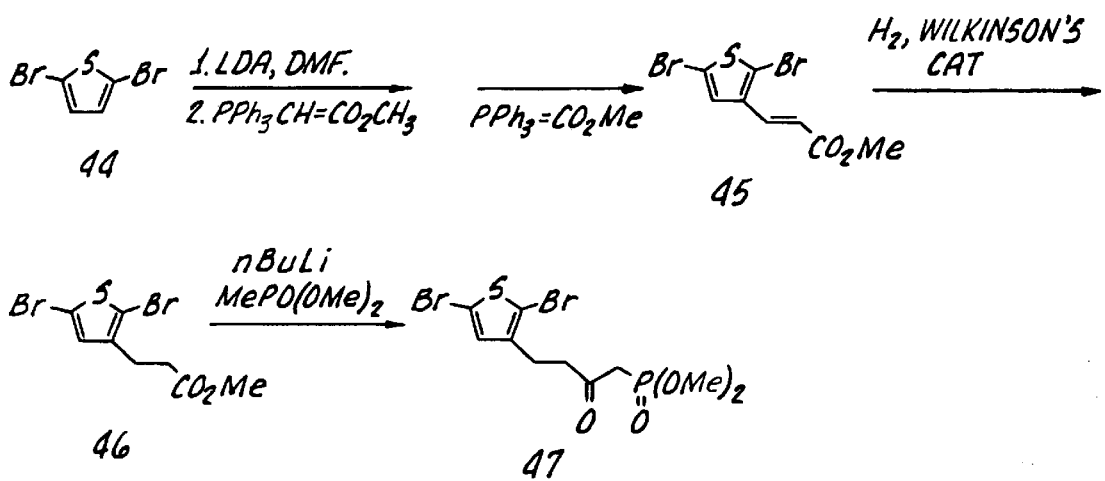
FIG. 4 is a schematic of the chemical synthesis of certain intermediates useful in preparing the compound of Example 43, below.
Figure 5A:
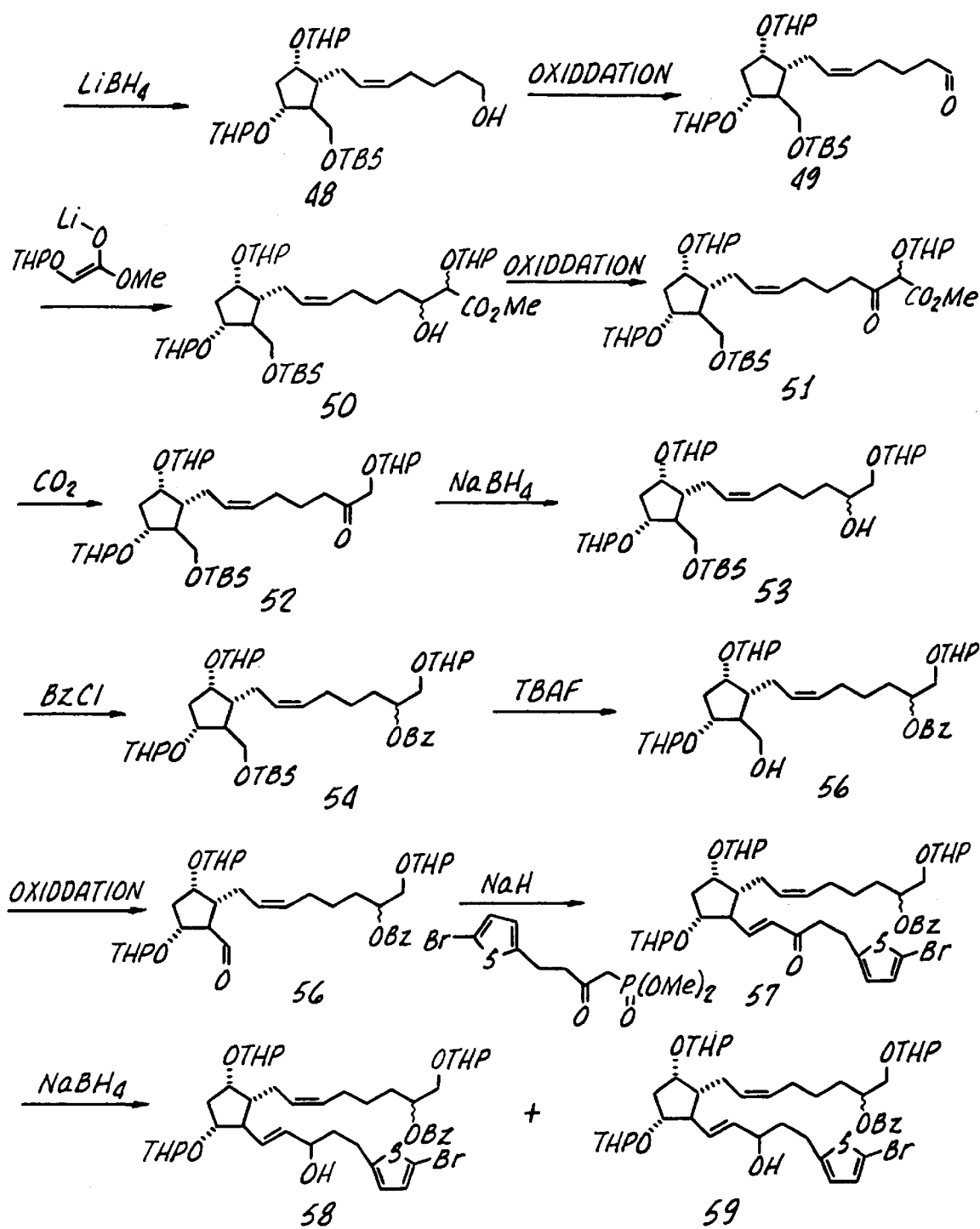
FIG. 5 is a schematic of the chemical synthesis of certain compounds of the present invention, in particular the compound of Example 63, below.
Figure 5B:
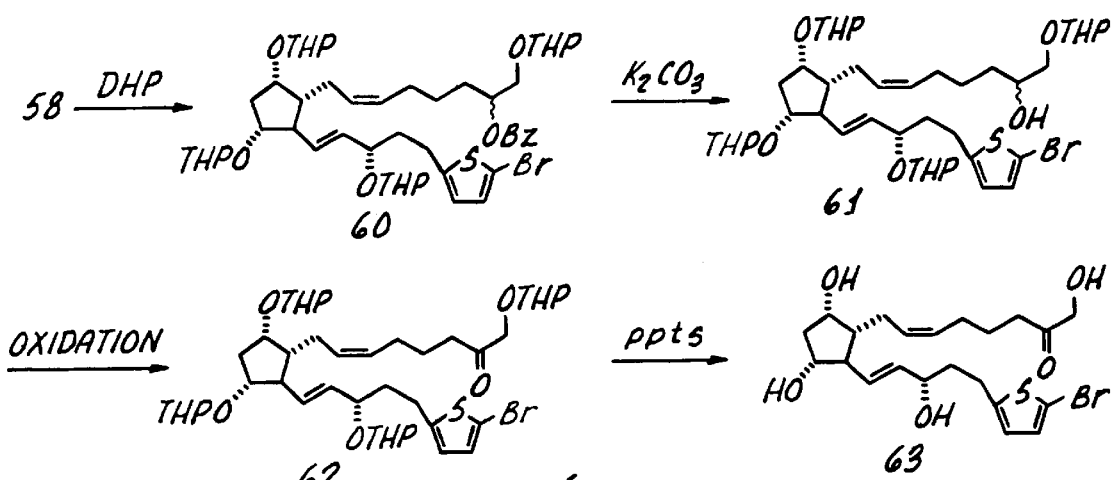
Figure 6:
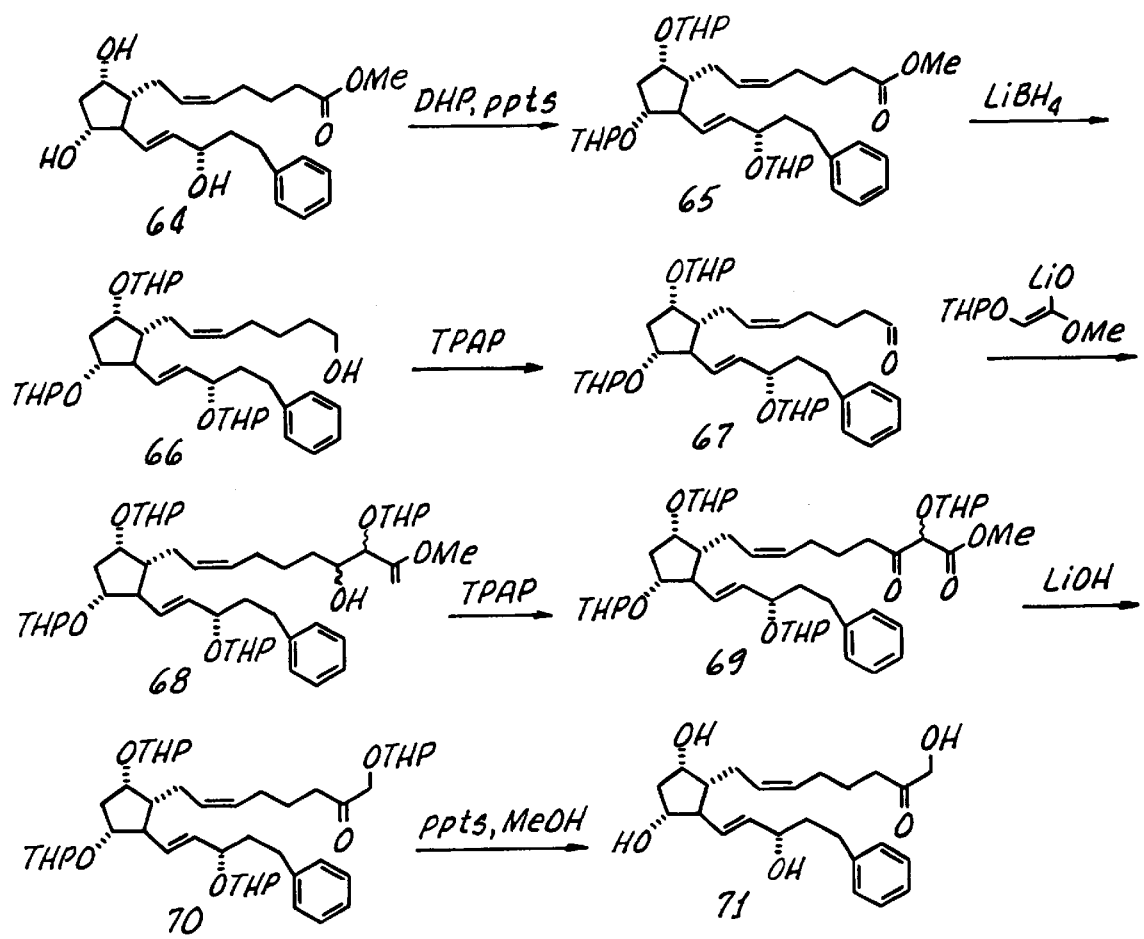
FIG. 6 is a schematic of the chemical synthesis of certain compounds of the present invention, in particular the compound of Example 71, below.
Figure 7:
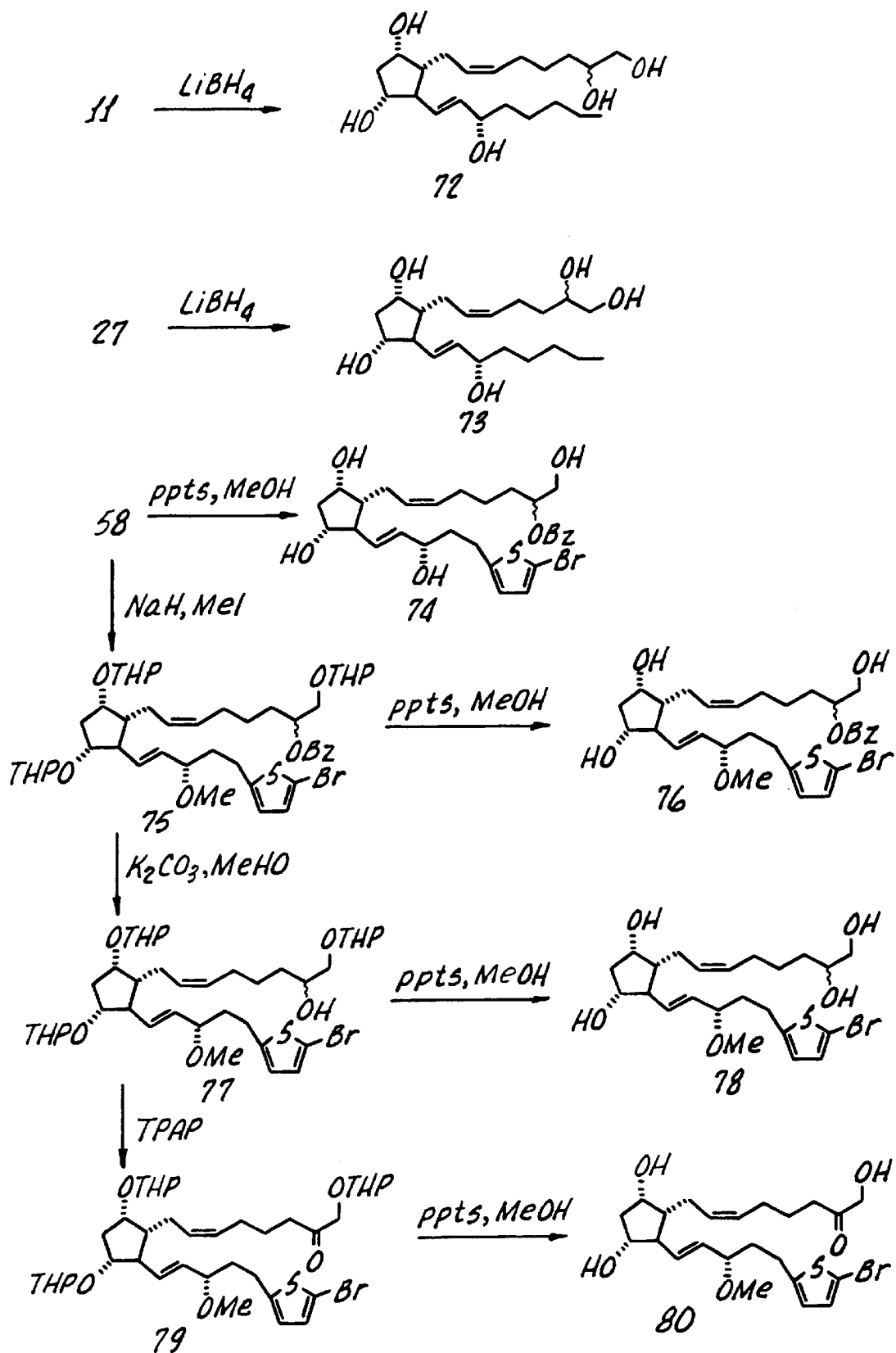
FIG. 7 is a schematic of the chemical synthesis of certain compounds of the present invention, in particular the compound of Examples 72, 73, 74, 76, 78 and 80, below.
Figure 8:
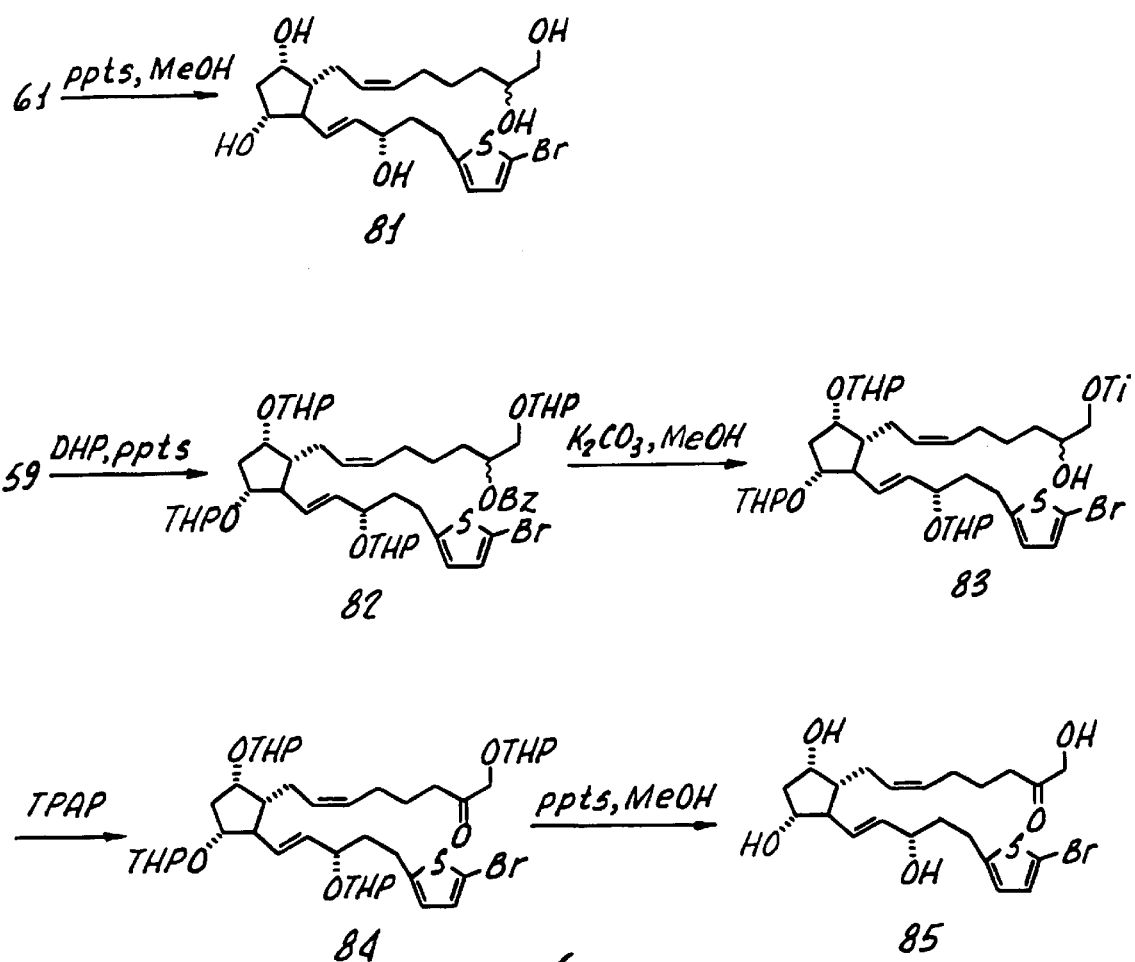
FIG. 8 is a schematic of the chemical synthesis of certain compounds of the present invention, in particular the compound of Examples 81 and 85, below.

The present invention relates to the use of cyclopentane 1-hydroxy alkyl or alkenyl-2-one or 2-hydroxy derivatives as therapeutic agents, e.g. as ocular hypotensives. The compounds used in accordance with the present invention are encompassed by the following structural formula I:

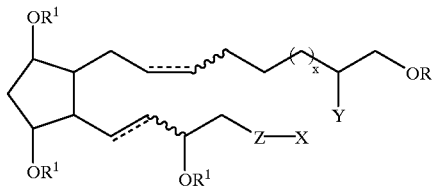

wherein R is H or $COR^3$;
  $R^1$ is H, $R^2$, phenyl, or $COR^3$, wherein $R^2$ is $C_1$–$C_5$ lower alkyl and $R^3$ is $R^2$ or phenyl;
  Z is $CH_2$ or O;
  Y is OH, $OCOR^3$ or =O;
  x is 0 or 1; and
  X is $C_1$–$C_5$ n-alkyl, $C_3$–$C_7$ cycloalkyl, phenyl, furanyl, thienyl or substituted derivatives thereof, wherein the substituents maybe selected from the group consisting of $C_1$–$C_5$ alkyl, halogen, $CF_3$, CN, $NO_2$, $NR^4_2$, $CO_2R^4$ and $OR^4$ wherein
    $R^4$ is hydrogen or $C_1$–$C_5$ alkyl and dotted lines represent the presence or absence of a double bond and wavy lines represent a cis or trans bond.

A preferred group of the compounds of the present invention includes compounds that have the following structural formula II:

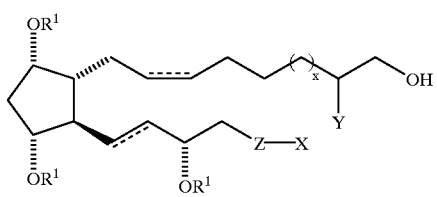

wherein the substituents and symbols are as hereinabove defined. In particular, the dotted lines on bonds between carbons 5 and 6 (C-5) and carbons 13 and 14 (C-13) indicate a single or double bond. If two solid lines are used at C-5, or C-13, it indicates a specific configuration for that double bond. Hatched lines used at position C-8, C-9 and C-11 indicate the α configuration. A triangle at position C-12 represents β orientation.

Another preferred group includes compounds having the formula III:

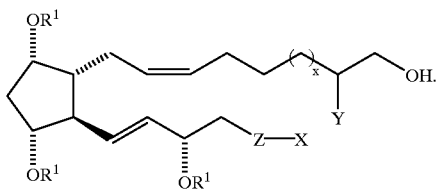

Preferably R is H.
Preferably $R^1$ is H or $CH_3$.
Preferably Y is OH or =O.
Preferably X is selected from the group consisting of n-propyl, phenyl and mono and dibromothienyl.

In the above formulae, the substituents and symbols are as hereinabove defined.

The above compounds of the present invention may be prepared by methods that are known in the art or according to the working examples below. The compounds, below, are especially preferred representative of the compounds of the present invention.

(Z)-8-[1R,2R,3R,5S)-3,5-Dihydroxy-2-((S)-(E)-3-hydroxyoct-1-enyl)-cyclopentyl]-1-hydroxyoct-6-en-2-one.

(Z)-7-[1R,2R,3R,5S)-3,5-Dihydroxy-2-((S)-(E)-3-hydroxyoct-1-enyl)-cyclopentyl]-1-hydroxyhept-5-en-2-one.

(Z)-8-{(1R,2R,3R,5S)-2-[(S)-(E)-5-(2,5-Dibromothiophen-3-yl)-3-hydroxy-pent-1-enyl]-3,5-dihydroxycyclopentyl}-1-hydroxyoct-6-en-2-one.

(Z)-8-{(1R,2R,3R,5S)-2-[(S)-(E)-5-(5-Bromothiophen-2-yl)-3-hydroxy-pent-1-enyl]-3,5-dihydroxycyclopentyl}-1-hydroxyoct-6-en-2-one (Z)-8-[(1R,2R,3R,5S)-3,5-Dihydroxy-2-((S)-(E)-3-hydroxy-5-phenylpent-1-enyl)cyclopentyl]-1-hydroxyoct-6-en-2-one Benzoic acid (Z)-7-{(1R,2R,3R,5S)-2-[(S)-(E)-5-(5-bromothiophen-2-yl)-3-methoxypent-1-enyl]-3,5-dihydroxycyclopentyl}-1-hydroxymethylhept-5-enyl ester (1S,3R,4R,5R)-4-[(S)-(E)-5-(5-Bromothiophen-2-yl)-3-methoxypent-1-enyl]-5-((Z)-7,8-dihydroxyoct-2-enyl) cyclopentane-1,3-diol (Z)-8-{(1R,2R,3R,5S)-2-[(S)-(E)-5-(5-Bromothiophen-2-yl)-3-methoxy-pent-1-enyl]-3,5-dihydroxycyclopentyl}-1-hydroxyoct-6-en-2-one (1S,3R,4R,5R)-4-[(S)-(E)-5-(5-Bromothiophen-2-yl)-3-hydroxypent-1-enyl]-5-((Z)-7,8-dihydroxyoct-2-enyl) cyclopentane-1,3-diol (Z)-8-{(1R,2R,3R,5S)-2-[(R)-(E)-5-(5-Bromothiophen-2-yl)-3-hydroxy-pent-1-enyl]-3,5-dihydroxycyclopentyl}-1-hydroxyoct-6-en-2-one Benzoic acid (Z)-7-{(1R,2R,3R,5S)-2-[(S)-(E)-5-(5-bromothiophen-2-yl)-3-hydroxypent-1-enyl]-3,5-dihydroxycyclopentyl}-1-hydroxymethyl-hept-5-enyl ester Benzoic acid (Z)-7-{(1R,2R,3R,5S)-2-[(S)-(E)-5-(5-bromothiophen-2-yl)-3-methoxypent-1-enyl]-3,5-dihydroxycyclopentyl}-1-hydroxymethylhept-5-enyl ester (1S,3R,4R,5R)-4-[(S)-(E)-5-(5-Bromothiophen-2-yl)-3-methoxypent-1-enyl]-5-((Z)-7,8-dihydroxyoct-2-enyl) cyclopentane-1,3-diol (Z)-8-{(1R,2R,3R,5S)-2-[(S)-(E)-5-(5-Bromothiophen-2-yl)-3-methoxy-pent-1-enyl]-3,5-dihydroxycyclopentyl}-1-hydroxyoct-6-en-2-one (1S,3R,4R,5R)-4-[(S)-(E)-5-(5-Bromothiophen-2-yl)-3-methoxypent-1-enyl]-5-((Z)-7,8-dihydroxyoct-2-enyl) cyclopentane-1,3-diol (Z)-8-{(1R,2R,3R,5S)-2-[(S)-(E)-5-(5-Bromothiophen-2-yl)-3-methoxy-pent-1-enyl]-3,5-dihydroxycyclopentyl}-1-hydroxyoct-6-en-2-one Benzoic acid (Z)-7-{(1R,2R,3R,5S)-2-[(S)-(E)-5-(4-chloro-5-methyl-thiophen-2-yl)-3-hydroxy-pent-1-enyl]-3,5-dihydroxy-cyclopentyl}-1-hydroxymethyl-hept-5-enyl ester (1S,3R,4R,5R)-4-[(S)-(E)-5-(4-Chloro-5-methyl-thiophen-2-yl)-3-methoxy-pent-1-enyl]-5-((Z)-7,8-dihydroxy-oct-2-enyl)-cyclopentane-1,3-diol (1S,3R,4R,5R)-4-[(S)-(E)-5-(4-Chloro-5-methyl-thiophen-2-yl)-3-hydroxy-pent-1-enyl]-5-((Z)-7,8-dihydroxy-oct-2-enyl)-cyclopentane-1,3-diol (Z)-8-{(1R,2R,3R,5S)-2-[(S)-(E)-5-(4-Chloro-5-methyl-thiophen-2-yl)-3-hydroxy-pent-1-enyl]-3,5-dihydroxy-cyclopentyl}-1-hydroxy-oct-6-en-2-one (Z)-8-{(1R,2R,3R,5S)-2-[(R)-(E)-5-(4-Chloro-5-methyl-thiophen-2-yl)-3-hydroxy-pent-1-enyl]-3,5-dihydroxy-cyclopentyl}-1-hydroxy-oct-6-en-2-one Benzoic acid (Z)-7-{(1R,2R,3R,5S)-3,5-dihydroxy-2-[(S)-(E)-3-hydroxy-5-(5-methyl-thiophen-2-yl)-pent-1-enyl]-cyclopentyl}-1-hydroxymethyl-hept-5-enyl ester (1R,3S,4R,5R)-4-((Z)-7,8-Dihydroxy-oct-2-enyl)-5-[(S)-(E)-3-hydroxy-5-(5-methyl-thiophen-2-yl)-pent-1-enyl]-cyclopentane-1,3-diol (Z)-8-{(1R,2R,3R,5S)-3,5-Dihydroxy-2-[(S)-(E)-3-methoxy-5-(5-methyl-hiophen-2-yl)-pent-1-enyl]-cyclopentyl}-1-hydroxy-oct-6-en-2-one (Z)-8-{(1R,2R,3R,5S)-3,5-Dihydroxy-2-[(S)-(E)-3-hydroxy-5-(5-methyl-thiophen-2-yl)-pent-1-enyl]-cyclopentyl}-1-hydroxy-oct-6-en-2-one (1S,3R,4R,5R)-4-[(S)-(E)-5-(5-Chloro-thiophen-2-yl)-3-methoxy-pent-1-enyl]-5-((Z)-7,8-dihydroxy-oct-2-enyl)-cyclopentane-1,3-diol (1S,3R,4R,5R)-4-[(S)-(E)-5-(5-Chloro-thiophen-2-yl)-3-hydroxy-pent-1-enyl]-5-((Z)-7,8-dihydroxy-oct-2-enyl)-cyclopentane-1,3-diol (1S,3R,4R,5R)-4-[(R)-(E)-5-(5-Chloro-thiophen-2-yl)-3-hydroxy-pent-1-enyl]-5-((Z)-7,8-dihydroxy-oct-2-enyl)-cyclopentane-1,3-diol (Z)-8-{(1R,2R,3R,5S)-2-[(S)-(E)-5-(5-Chloro-thiophen-2-yl)-3-methoxy-pent-1-enyl]-3,5-dihydroxy-cyclopentyl}-1-hydroxy-oct-6-en-2-one (Z)-8-{(1R,2R,3R,5S)-2-[(S)-(E)-5-(5-Chloro-thiophen-2-yl)-3-hydroxy-pent-1-enyl]-3,5-dihydroxy-cyclopentyl}-1-hydroxy-oct-6-en-2-one (Z)-8-{(1R,2R,3R,5S)-2-[(R)-(E)-5-(5-Chloro-thiophen-2-yl)-3-hydroxy-pent-1-enyl]-3,5-dihydroxy-cyclopentyl}-1-hydroxy-oct-6-en-2-one Acetic acid (Z)-8-{(1R,2R,3R,5S)-2-[(S)-(E)-5-(5-chloro-thiophen-2-yl)-3-hydroxy-pent-1-enyl]-3,5-dihydroxy-cyclopentyl}-2-oxo-oct-6-enyl ester Acetic acid (Z)-8-{(1R,2R,3R,5S)-3-acetoxy-2-[(S)-(E)-5-(5-chloro-thiophen-2-yl)-3-hydroxy-pent-1-enyl]-5-hydroxy-cyclopentyl}-2-oxo-oct-6-enyl ester Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples, which are summarized in the reaction schemes of FIGS. 1 through 4, wherein the compounds are identified by the same designator in both the Examples and the Figures.

EXAMPLE 1

(Z)-7-[(1R,2R,3R,5S)-3,5-Dihydroxy-2-((S)-(E)-3-hydroxyoct-1-enyl)-cyclopentyl]hept-5-enoic Acid $PGF_{2\alpha}$ was obtained from Dinoprost Tromethamine USP by dissolution of the salt in 1N HCl and extracting three times with ethylacetate (EtOAc (3×)), followed by washing the combined organic phase with brine and drying over $Na_2SO_4$. After removal of solvent, this process afforded 4.98 g of acid from 6.24 g of the corresponding salt.

EXAMPLE 2

(Z)-7-[(1R,2R,3R,5S)-3,5-Dihydroxy-2-((S)-(E)-3-hydroxyoct-1-enyl)-cyclopentyl]hept-5-enoic Acid Methyl Ester The acid was then dried overnight via hi-vacuum, and dissolved in N,N-dimethyl formamide (DMF) (50 mL). Iodomethane (4.00 g, 28.1 mmol) and $K_2CO_3$ (3.88 g, 28.1 mmol) were added and the mixture stirred at 23° C. for 6 h. The DMF was evaporated and the residue partitioned between saturated aqueous $NH_4Cl$ and $CH_2Cl_2$ and separated. The aqueous phase was washed with $CH_2Cl_2$ (4×) and the combined organics were dried ($MgSO_4$) and concentrated in vacuo to afford 4.79g of the named compound.

EXAMPLE 3

(Z)-7-{(1R,2R,3R,5S)-3-(tert-Butyldimethylsilanyloxy)-2-[(S)-(E)-3-(tert-butyl-dimethylsilanyloxy)oct-1-enyl]-5-[(dimethylethyl) dimethylsilanyloxy]-cyclopentyl}hept-5-enoic Acid Methyl Ester The triol of Example 2 (4.79 g, 13.02 mmol), tert-butyldimethylsilyl chloride (7.8 g, 52.08 mmol), imidazole (7.07 g, 104 mmol), and 4-(Dimethylamino)pyridine (DMAP) (122 mg) were dissolved in DMF (100 mL) and stirred at 23° C. for 48 h.

The mixture was concentrated, dissolved in $CH_2Cl_2$ and washed with cold 1% HCl, saturated aqueous $NaHCO_3$ and dried ($Na_2SO_4$). Separation by flash column chromatography (FCC) (silica gel, 5% EtOAc/hex) afforded 8.63 g of the above named ester.

EXAMPLE 4

(Z)-7-{(1R,2R,3R,5S)-3-(tert-Butyldimethylsilanyloxy)-2-[(S)-(E)-3-(tert-butyl-dimethylsilanyloxy)oct-1-enyl-]-5-[(ethyl) dimethylsilanyloxy]cyclopentyl}hept-5-enoic Acid To a mixture of the ester of Example 3 (500 mg, 0.704 mmol), tetrahydrofuran (THF) and water was added LiOH (5.64 mL of a 0.5 M solution in H2O, 2.82 mmol) and the reaction stirred for 48 h at 23° C. The THF was evaporated, and the organic phase was acidified with dilute HCl then extracted with EtOAc (2×). The combined organics were washed with brine, dried ($Na_2SO_4$), filtered and concentratred in vacuo to afford 0.515 g of the above named acid.

EXAMPLE 5

(Z)-7-{(1R,2R,3R,5S)-3-(tert-Butyldimethylsilanyloxy)-2-[(S)-(E)-3-(tert-butyl-dimethylsilanyloxy)oct-1-enyl]-5-[(dimethylethyl)dimethylsilanyloxy]-cyclopentyl}hept-5-enoic Acid Methoxymethylamide After the acid of Example 4 (0.489 g, 0.704 mmol), $CH_2Cl_2$ (5 mL) and triethylamine ($Et_3N$) (214 mg, 2.11 mmol) were combined and cooled to 0° C. Ethyl chloroformate (91.7 mg, 0.845 mmol) was added and stirring was continued for another 15 min. N,N-Dimethylhydroxylamine hydrochloride (82.3 mg, 0.845 mmol) and the reaction stirred at 0° C. for 1 h and 23° C. for 3 h. The reaction was washed with 5% HCl, saturated aqueous $NaHCO_3$ and dried ($Na_2SO_4$). FCC (silica gel, 20% EtOAc/hex) gave 0.499 g of the above named amide.

EXAMPLE 6

(Z)-8-{(1R,2R,3R,5S)-3-(tert-Butyldimethylsilanyloxy)-2-[(S)-(E)-3-(tert-butyl-dimethylsilanyloxy)oct-1-enyl]-5-[(dimethylethyl)dimethylsilanyloxy]-cyclopentyl}oct-6-en-2-one The N,N-methoxymethyl amide of Example 5 (100 mg, 0.135 mmol) was dissolved in THF (1 mL) and cooled to 0° C. Methylmagnesium bromide (0.14 mL, 3 M in $Et_2O$, 0.42 mmol)) was added and the reaction stirred at 0° C. for 2 h. The reaction was then quenched by addition of saturated aqueous $NH_4Cl$ and the reaction stirred 20 min at 23° C. $Et_2O$ was added and the mixture was partitioned. The organic layer was washed with brine, dried ($Na_2SO_4$), filtered and concentrated in vacuo. FCC (silica gel, 5% EtOAc/hex) afforded 75 mg of the above named ketone.

EXAMPLE 7

(1R,2R,3R,4S)-1-(tert-Butyldimethylsilanyloxy)-3-[(Z)-7-(tert-butyldimethyl-silanyloxy)octa-2,7-dienyl]-2-[(S)-(E)-3-(tert-butyldimethylsilanyloxy)oct-1-enyl]-4-[(dimethylethyl)dimethylsilanyloxy]cyclopentane To a solution of the ketone (42.8 g, 0.0592 mmol), $CH_2Cl_2$ (2 mL) and N,N-diisopropylethylamine (0.306 g, 2.37 mmol) was added tert-Butyldimethylsilyl-trifluoromethane sulfonate (0.235 g, 0.888 mmol). The reaction mixture was stirred 10 min at 0° C., then concentrated and partitioned between $Et_2O$ and saturated aqueous $NaHCO_3$. The organic layer was separated and was washed with saturated aqueous $NaHCO_3$ (2×), dried ($Na_2SO_4$) filtered and concentrated in vacuo to afford 44.2 mg of the above named silyl enol ether.

EXAMPLE 8

(Z)-1-Bromo-8-{(1R,2R,3R,5S)-3-(tert-butyldimethylsilanyloxy)-2-[(S)-(E)-3-(tert-butyldimethylsilanyloxy)oct-1-enyl]-5-[(dimethylethyl)dimethylsilanyloxyl]-cyclopentyl}oct-sen-2-one Silyl enol ether of Example 7(118.2 mg, 0.146 mmol), $NaHCO_3$ (18.0 mg, 0.22 mmol), and THF (2 mL) were combined and cooled to 0° C. N-Bromosuccinimide (26 mg, 0.146 mmol) was added followed by a second equivalent 2 h later. The reaction was stirred for another 1 h at 0° C. after which it was partitioned between saturated aqeous $NaHCO_3$ and $Et_2O$. The organic phase was separated, dried ($Na_2SO_4$), filtered and concentrated in vacuo. FCC (silica gel, 2% EtOAc/hex) afforded 83.1 mg of the above named bromide.

EXAMPLE 9

Acetic Acid (Z)-8-{(1R,2R,3R,5S)-3-(tert-butyldimethylsilanyloxy)-2-[(S)-(E)-3-(tert-butyldimethylsilanyloxy)oct-1-enyl]-5-[(dimethylethyl)dimethylsilanyloxy]-cyclopentyl}-2-oxo-oct-6-enyl Ester Bromide of Example 8 (74 mg, 0.1 mmol) was combined with NaOAc (82 mg, 1.0 mmol) in DMF (2 mL) and was stirred 12 h at 23° C. The DMF was evaporated and the mixture partitioned between $CH_2Cl_2$ and water. The organic phase was dried ($Na_2SO_4$) filtered and concentrated in vacuo. FCC (silica gel, 5% EtOAc/hex) provided 51 mg of the above named acetate.

EXAMPLE 10

Acetic Acid (Z)-8-[(1R,2R,3R,5S)-3,5-dihydroxy-2-((S)-(E)-3-hydroxyoct-1-enyl)-cyclopentyl]-2-oxo-oct-6-enyl Ester Acetate of Example 9 (46 mg, 0.061 mmol), THF (0.5 mL) and hydrogen fluoride-pyridine (1 mL) were combined in a plastic vial and stirred for 20 h. The reaction was neutralized with saturated aqueous $Na_2CO_3$ and was extracted with EtOAc. The organic phase was dried ($Na_2SO_4$), filtered and concentrated in vacuo. FCC (silica gel, 10% MeOH/EtOAc) provided 21 mg of the above named triol as a clear colorless oil.

EXAMPLE 11

(Z)-8-[(1R,2R,3R,5S)-3,5-Dihydroxy-2-((S)-(E)-3-hydroxyoct-1-enyl)-cyclopentyl]-1-hydroxyoct-6-en-2-one The acetate of Example 10 (2.1 mg, 0.005 mmol), saturated aqueous $Na_2CO_3$ and MeOH (1 mL) were combined and stirred at 23° C. for 4 h. The reaction was concentrated, diluted with EtOAc and filtered to obtain 0.8 mg of the above named ketone.

EXAMPLE 13

(3αR,4R,5R,6αS)-5-Hydroxy4-((S)-(E)-3-hydroxyoct-1-enyl)hexahydro-cyclopenta[b]furan-2-one

[(1R,2R,3R,5S)-3,5-Dihydroxy-2-((S)-(E)-3-hydroxyoct-1-enyl)cyclopentyl]acetic acid (3.0 g, 0.010 mol), 3N HCl (27 mL) and THF (54 mL) were stirred at 23° C. for 12 h. The reaction was diluted with EtOAc and partitioned. The organic phase was separated and was washed with water, brine, dried ($Na_2SO_4$), filtered and concentrated in vacuo to afford 3.08 g of the above named diol.

EXAMPLE 14

(3αR,4R,5R,6αS)-5-(Tetrahydropyran-2-yloxy)-4-[(S)-(E)-3-(tetrahydropyran-2-yloxy)oct-1-enyl]hexahydrocyclopenta[b]furan-2-one The crude diol of Example 13 (3.08 g, 0.011 mol), 3,4-dihydro-2H-pyran (2.78 g, 0.033 mol), $CH_2Cl_2$ (54 mL) and pyridiniump-toluenesulfonate (PPTs) (0.28 g, 0.0011 mol) were combined and stirred at 23° C. for 2 h. The reaction was concentrated, diluted with EtOAc and washed with 1 N HCl, saturated aqueous NaHCO$_3$ and brine. The organic portion was dried (Na$_2$SO$_4$), filtered and concentrated in vacuo to afford 4.21 g of the above named lactone.

EXAMPLE 15

(3αR,4R,5R,6αS)-5-(Tetrahydropyran-2-yloxy)-4-[(S)-(E)-3-(tetrahydropyran-2-yloxy)-oct-1-enyl]hexahydrocyclopenta[b]furan-2-ol Lactone of Example 14 (0.5 g, 1.15 mmol) in CH$_2$Cl$_2$ (5 mL) was cooled to −78° C. and DIBAL-H (2.3 mL, 1 M in CH$_2$Cl$_2$, 2.3 mmol) was added. The reaction stirred at −78° C. for 2 h and was quenched by dropwise addition of MeOH (1 mL). The mixture was allowed to warm to room temperature, 1N NaOH was added and the mixture was stirred for 1 h. The aqueous layer was separated and extracted with CH$_2$Cl$_2$ (2×). The combined organics were dried (Na$_2$SO$_4$), filtered and concentrated in vacuo to afford 0.45 g of the above named alcohol.

EXAMPLE 16

(Z)-6{(1R,2R,3R,5S)-5-Hydroxy-3-(tetrahydropyran-2-yloxy)-2-[(S)-(E)-3-(tetrahydropyran-2-yloxy)oct-1-enyl]cyclopentyl}-hex4-enoic Acid Potassium bis(trimethylsilyl)amide (48.4 mL, 0.5 M solution in toluene) was added to a suspension of 4-(carboxybutyl)triphenylphosphonium bromide in THF (40 mL) at 0° C. After 10 min the orange red mixture was cooled to −78° C. and the alcohol of Example 15 in THF (8 mL) was added rapidly. The reaction was allowed to slowly warm to 23° C. overnight and then was quenched with saturated aqueous NH$_4$Cl. The solvent was evaporated and the aqueous layer was extracted with EtOAc (5×). The combined organics were dried (Na$_2$SO$_4$), filtered and concentrated in vacuo to yield the above named acid.

EXAMPLE 17

(Z)-6-{(1R,2R,3R,5S)-5-Hydroxy-3-(tetrahydropyran-2-yloxy)-2-[(S)-(E)-3-(tetrahydropyran-2-yloxy)oct-1-enyl]cyclopentyl}-hex-4-enoic Acid Methyl Ester The acid of Example 16 was combined with iodomethane (2.0 mL, 32 mmol) and K$_2$CO$_3$ (4.42 g, 32 mmol) in DMF (30 mL) and was stirred 12 h at 23° C. The reaction was concentrated in vacuo and the residue partitioned between CH$_2$Cl$_2$ and saturated aqueous NH$_4$Cl. The organic portion was dried (Na$_2$SO$_4$), filtered and concentrated in vacuo. FCC (silica gel, 25% EtOAc/hex) afforded 2.65 g of the above named ester as a viscous yellow oil.

EXAMPLE 18

(Z)-6-{(1R,2R,3R,5S)-3,5-Bis-(tetrahydropyran-2-yloxy)-2-[(S)-(E)-3-(tetrahydro-pyran-2-yloxy)-oct-1-enyl]cyclopentyl}hex-4-enoic Acid Methyl Ester The ester of Example 17 is reacted in accordance with the process of Example 14 to yield the named ester.

EXAMPLE 19

(Z)-6-{(1R,2R,3R,5S)-3,5-Bis-(tetrahydropyran-2-yloxy)-2-[(S)-(E)-3-(tetrahydro-pyran-2-yloxy)oct-1-enyl]cyclopentyl}hex-4-en-1-ol The crude ester of Example 18 (2.97 g) was dissolved in Et$_2$O and LiBH$_4$ (216 mg, 9.8 mmol) was added. The reaction was stirred 16 h at 23° C. and three drops of water were added followed by 1N NaOH. The mixture was stirred 1 h, the Et$_2$O was evaporated and the aqueous phase was extracted with CH$_2$Cl$_2$ (3×). The organic phase was dried (Na$_2$SO$_4$) filtered and concentrated in vacuo. FCC (silica gel, 40% EtOAc/hex) afforded 1.77 g of the above named alcohol.

EXAMPLE 20

(Z)-6-{(1R,2R,3R,5S)-3,5-Bis-(tetrahydropyran-2-yloxy)-2-[(S)-(E)-3-(tetrahydro-pyran-2-yloxy)oct-1-enyl]cyclopentyl}hex-4-en-1-ol DMSO (0.19 g, 2.38 mmol) was added to oxalyl chloride (0.57 mL, 2M in CH$_2$Cl$_2$, 1.14 mmol) in CH$_2$Cl$_2$ (2.5 mL) at −78° C. and was stirred 15 min. A solution of the alcohol of Example 19 (549 mg, 0.95 mmol) in CH$_2$Cl$_2$ was added dropwise and stirring continued for 15 min at −78° C. Et$_3$N (0.77 g, 7.6 mmol) was added and the reaction was warmed to 23° C. After the mixture had stirred 1 h at 23° C., the mixture was washed with 1% HCl, saturated aqueous NaHCO$_3$ and brine. The organic portion was dried (Na$_2$SO$_4$), filtered and concentrated in vacuo. FCC (silica gel, 20% EtOAc/hex) afforded 198 mg of the above named aldehyde.

EXAMPLE 21

(Z)-7-{(1R,2R,3R,5S)-3,5-Bis-(tetrahydropyran-2-yloxy)-2-[(S)-(E)-3-(tetrahydro-pyran-2-yloxy)oct-1-enyl]cyclopentyl}hept-5-en-2-ol The aldehyde of Example 20 is reacted in accordance with the process of Example 6 to yield the named compound.

EXAMPLE 22

(Z)-7-{(1R,2R,3R,5S)-3,5-Bis-(tetrahydropyran-2-yloxy)-2-[(S)-(E)-3-(tetrahydro-pyran-2-yloxy)oct-1-enyl]cyclopentyl}hept-5-en-2-one The alcohol of Example 21 is reacted in accordance with the process of Example 20 to yield the named compound.

EXAMPLE 23

((Z)-6-{(1R,2R,3R,5S)-3,5-Bis-(tetrahydropyran-2-yloxy)-2-[(S)-(E)-3-(tetrahydro-pyran-2-yloxy)oct-1-enyl]cyclopentyl}-methylenehex-4-enyloxy)-tert-butyl-dimethylsilane The ketone of Example 22 is reacted in accordance with the process of Example 7 to yield the named compound.

EXAMPLE 24

(Z)-7-{(1R,2R,3R,5S)-3,5-Bis-(tetrahydropyran-2-yloxy)-2-[(S)-(E)-3-(tetrahydro-pyran-2-yloxy)oct-1-enyl]cyclopentyl}-1-bromohept-5-en-2-one The silyl enol ether of Example 23 is reacted in accordance with the process of Example 8 to yield the named compound.

EXAMPLE 25

Acetic Acid (Z)-7-{(1R,2R,3R,5S)-3,5-bis-(tetrahydropyran-2-yloxy)-2-[(S)-(E)-3-(tetrahydropyran-2-yloxy)oct-1-enyl]cyclopentyl}-2-oxohept-5-enyl Ester The bromide of Example 24 is reacted in accordance with the process of Example 9 to yield the named compound.

EXAMPLE 26

Acetic Acid (Z)-7-[(1R,2R,3R,5S)-3,5-dihydroxy-2-((S)-(E)-3-hydroxyoct-1-enyl)-cyclopentyl]-2-oxohept-5-enyl Ester A solution of the acetate of Example 25 (36 mg, 0.055 mmol) and PPTs (2 mg) in MeOH (1.0 mL) was stirred at 45° C. for 4 h. The reaction was cooled to room temperature and the solvent was removed in vacuo. The residue was diluted with EtOAc and washed with 1N HCl, saturated aqueous NaHCO$_3$ and brine. The organic portion was dried (MgSO$_4$), filtered and concentrated in vacuo. FCC (silica gel, 50%–100% EtOAc/hex) afforded 18 mg of the named compound.

EXAMPLE 27

(Z)-7-[(1R,2R,3R,5S)-3,5-Dihydroxy-2-((S)-(E)-3-hydroxyoct-1-enyl)-cyclopentyl]-1-hydroxyhept-5-en-2-one The acetate of Example 26 is reacted in accordance with the process of Example 11 to yield the named compound.

EXAMPLE 29

(Z)-7-[(1R,2S,3R,5S)-2-(tert-Butyldimethylsilanyloxymethyl)-3,5-bis-(tetrahydro-pyran-2-yloxy)cyclopentyl]hept-5-enoic Acid To (Z)-7-[(1R,2S,3R,5S)-2-(tert-Butyldimethylsilanyloxymethyl)-3,5-bis-(tetrahydropyran-2-yloxy)cyclopentyl]hept-5-enoic acid methyl ester (1.5 g, 2.71 mmol) stirring in THF was added LiOH (4 mL, 1M in H$_2$O, 4.0 mmol) and the stirring was continued at 23° C. for 12 h. The THF was evaporated and the mixture was acidified with cold 1% HCl and extracted with CH$_2$Cl$_2$ (3×). The combined organics were washed with brine, dried (Na$_2$SO$_4$) filtered and concentrated in vacuo. FCC (silica gel, 30% EtOAc/hex) afforded 1.23 g of the above named acid.

EXAMPLE 30

(Z)-7-[(1R,2S,3R,5S)-2-(tert-Butyldimethylsilanyloxymethyl)-3,5-bis-(tetrahydro-pyran-2-yloxy)cyclopentyl]hept-5-enoic Acid Methoxymethylamide The acid of Example 29 is reacted in accordance with the process of Example 5 to yield the named compound.

EXAMPLE 31

(Z)-8-[(1R,2S,3R,5S)-2-(tert-Butyldimethylsilanyloxymethyl)-3,5-bis-(tetrahydro-pyran-2-yloxy)cyclopentyl]oct-6-en-2-one The amide of Example 30 is reacted in accordance with the process of Example 6 to yield the named compound.

EXAMPLE 32

(Z)-8-[(1R,2S,3R,5S)-2-(tert-Butyldimethylsilanyloxymethyl)-3,5-bis-(tetrahydro-pyran-2-yloxy)cyclopentyl]-1-hydroxyoct-6-en-2-one To the ketone of Example 31 (1.0 g, 1.76 mmol) in THF (50 mL) cooled to −78° C. was added sodium bis(trimethylsilyl)amide (2.64 mL, 1M in THF). The mixture was stirred at −78° C. for 15 min, after which rac-camphorsulfonyloxaziridine (1.21 g, 5.28 mmol) in THF (10 mL) was added rapidly. The reaction was stirred 1 h at −78° C. and was quenched with saturated aqueous NH$_4$Cl. The mixture was warmed to 23° C., the THF removed by evaporation and Et$_2$O was added. The imine and oxaziridine biproducts were filtered off, and the filtrate was concentrated in vacuo. This Et$_2$O addition/filtration process was repeated 3× to remove most of the remaining imine and oxaziridine biproducts. FCC (silica gel, 20% EtOAc/hex) afforded 0.48 g of the above named hydroxy ketone.

EXAMPLE 33

(Z)-8-[(1R,2S,3R,5S)-2-(tert-Butyldimethylsilanyloxymethyl)-3,5-bis-(tetrahydro-pyran-2-yloxy)cyclopentyl]-1-(tetrahydropyran-2-yloxy)oct-6en-2-one The alcohol of Example 32 (480 mg, 0.82 mmol), CH$_2$Cl$_2$ (5 mL), 3,4-Dihydro-2H-pyran (104 mg, 1.23 mmol) and PPTs (2 mg) were combined and stirred overnight at 23° C. The reaction was concentrated in vacuo. FCC (silica gel, 10% EtOAc/hex) afforded 374 mg of the above named ketone.

EXAMPLE 34

(Z)-8-[(1R,2S,3R,5S)-2-(tert-Butyldimethylsilanyloxymethyl)-3,5-bis-(tetrahydro-pyran-2-yloxy)cyclopentyl]-1-(tetrahydropyran-2-yloxy)oct-6-en-2-ol To the ketone of Example 33 (374 mg, 0.59 mmol) dissolved in ethanol (EtOH) (5 mL was added NaBH$_4$ (67 mg, 1.77 mmol) and the reaction was stirred 1 h at 23° C. Saturated aqueous NH$_4$Cl was added to quench the reaction and this mixture was stirred an additional 20 min. The EtOH was evaporated, and the mixture was extracted with CH$_2$Cl$_2$ (3×). The combined organics were washed with brine and dried (Na$_2$SO$_4$) filtered and concentrated in vacuo. FCC (silica gel, 10–20% EtOAc:/hex) afforded 320 mg of the above alcohol.

EXAMPLE 35

Benzoic acid (Z)-7-[(1R,2S,3R,5S)-2-(tert-butyldimethylsilanyloxymethyl)-3,5-bis-(tetrahydropyran-2-yloxy)cyclopentyl]-1-(tetrahydropyran-2-yloxymethyl)hept-5-enyl Ester The alcohol of Example 34 (320 mg, 0.5 mmol) was combined with pyridine (198 mg, 2.5 mmol) in CH$_2$Cl$_2$ (5 mL). To this mixture was added benzoyl chloride (BzCl) (141 mg, 1.0 mmol) at 0° C. and the mixture was allowed to warm to room temperature overnight. The reaction was diluted with CH$_2$Cl$_2$ and was washed with saturated aqueous NaHCO$_3$, saturated aqueous CuSO$_4$ and brine. FCC (silica gel, 10% EtOAc/hex) afforded the desired benzoate contaminated with benzoic acid (BzOH).

EXAMPLE 36

Benzoic Acid (Z)-7-[(1R,2S,3R,5S)-2-hydroxymethyl-3,5-bis-(tetrahydropyran-2-yloxy)cyclopentyl]-1-(tetrahydropyran-2-yloxymethyl)hept-5-enyl Ester To the benzoate of Example 35 in THF (4 mL) was added tetrabutylammonium fluoride (TBAF) (1 mL, 1M in THF)

and the reaction was stirred overnight at 23° C. The THF was then evaporated, and the mixture was partitioned between $CH_2Cl_2$ and 10% HCl. The organic phase was separated and washed with saturated aqueous $NaHCO_3$, brine, dried ($Na_2SO_4$), filtered and concentrated in vacuo. $^1H$ NMR analysis of the crude mixture indicated the presence of starting material, so the mixture was treated again with TBAF overnight. Usual work up conditions afforded 200 mg of the desired alcohol after FCC (silica gel, 20% EtOAc/hex) as a colorless oil.

EXAMPLE 37

Benzoic Acid (Z)-7-[(1R,2R,3R,5S)-2-formyl-3,5-bis-(tetrahydropyran-2-yloxy)-cyclopentyl]-1-(tetrahydropyran-2-yloxymethyl)hept-5-enyl Ester The alcohol of Example 36 is reacted in accordance with the process of Example 20 to yield the named compound.

EXAMPLE 38

Benzoic Acid (Z)-7-[(1R,2R,3R,5S)-2-[(E)-5-(2,5-dibromothiophen-3-yl)-3-oxo-pent-1-enyl]-3,5-bis-(tetrahydropyran-2-yloxy)cyclopentyl]-1-(tetrahydropyran-2-yloxymethyl)hept-5-enyl Ester A solution of the phosphonate of Example 48 below, (250 mg, 0.6 mmol) in THF (2 mL) was added to a suspension of NaH (11 mg, 0.44 mmol) in THF (2 mL) at 0° C. After 15 min a solution of the aldehyde of Example 37 (180 mg, 0.29 mmol) in THF (2 mL) was added, stirring was continued for 30 min and then the reaction was warmed to 23° C. The reaction was quenched with saturated aqueous $NH_4Cl$ and the THF was evaporated. The mixture was extracted with $CH_2Cl_2$ (3x), and the combined organics were washed with brine, dried ($Na_2SO_4$) and concentrated in vacuo. FCC (silica gel, 20% EtOAc/hex) afforded 120 mg of the above named ketone.

EXAMPLE 39

Benzoic Acid (Z)-7-[(1R,2R,3R,5S)-2-[(S)-(E)-5-(2,5-dibromothiophen-3-yl)-3-hydroxypent-1-enyl]-3,5-bis-(tetrahydropyran-2-yloxy)cyclopentyl]-1-(tetrahydro-pyran-2-yloxymethyl)hept-5-enyl Ester The ketone of Example 38 (120 mg, 0.13 mmol) is reacted in accordance with the process of Example 34 to yield the named compound (40 mg, lower $R_f$) along with its C(15) epimer (40 mg, higher $R_f$).

EXAMPLE 40

Benzoic Acid (Z)-7-[(1R,2R,3R,5S)-2-[(S)-(E)-5-(2,5-dibromothiophen-3-yl)-3-(tetrahydropyran-2-yloxy)pent-1-enyl]-3,5-bis-(tetrahydropyran-2-yloxy)-cyclopenty]-1-(tetrahydropyran-2-yloxymethyl)hept-5-enyl Ester The alcohol of Example 39 is reacted in accordance with the process of Example 14 or 33 to yield the named compound.

EXAMPLE 41

(Z)-8-[(1R,2R,3R,5S)-2-[(S)-(E)-5-(2,5-Dibromothiophen-3-yl)-3-(tetrahydro-pyran-2-yloxy)pent-1-enyl]-3,5-bis-(tetrahydropyran-2-yloxy)cyclopentyl]-1-(tetrahydropyran-2-yloxy)oct-6-en-2-ol The benzoate (42 mg, 0.042 mmol) of Example 40 was dissolved in MeOH (5 mL) and $K_2CO_3$ (14 mg, 0.10 mmol) was added. The reaction was stirred 12 h at 23° C. and the MeOH was removed in vacuo. The mixture was partitioned between $H_2O$ and $CH_2Cl_2$ and separated. The aqueous phase was extracted with $CH_2Cl_2$ (2x) and the combined organics were washed with brine, dried ($Na_2SO_4$), filtered and concentrated in vacuo. FCC (silica gel, 30% EtOAc/hex) afforded 28 mg of the above named alcohol.

EXAMPLE 42

(Z)-8-[(1R,2R,3R,5S)-2-[(S)-(E)-5-(2,5-Dibromothiophen-3-yl)-3-(tetrahydro-pyran-2-yloxy)-pent-1-enyl]-3,5-bis-(tetrahydropyran-2-yloxy)cyclopentyl]-1-(tetrahydropyran-2-yloxy)oct-6-en-2-one To a mixture of alcohol of Example 41 (28 mg, 0.03 1 mmol), 4-Methylmorpholine N-oxide (11 mg, 0.093 mmol) and 4 Å sieves (beads) was added tetrapropylammonium perruthenate (1 mg, 0.0031 mmol) at 23° C. and the reaction mixture stirred for 1 h when it was judged complete by TLC. The liquid component was decanted from the sieves, concentrated in vacuo. FCC (silica gel, 20% EtOAc/hex) afforded 20 mg of the above named ketone.

EXAMPLE 43

(Z)-8-{(1R,2R,3R,5S)-2-[(S)-(E)-5-(2,5-Dibromothiophen-3-yl)-3-hydroxypent-1-enyl]-3,5-dihydroxycyclopentyl}-1-hydroxyoct-6-en-2-one The ketone of Example 42 is reacted in accordance with the process of Example 26 to yield the named compound.

EXAMPLE 45

(E)-3-(2,5-Dibromothiophene-3-yl)acrylic Acid Methyl Ester

To 2,5-Dibromothiophene (1.5 g, 6.2 mmol in THF (30 mL) cooled to −78° C. was added lithium diisopropylamide (6.2 mL, 6.2 mmol; 1.0M in THF, 6.2 mmol;) dropwise. The mixture was stirred 5 min, and was quenched with DMF (1.4 g, 18.6 mmol). Stirring was continued for 15 min at −78° C. and water was added. The THF was evaporated, $Et_2O$ was added and the organic phase was separated and washed with water, 1% HCl, water (3x) and brine. The organic phase was passed through a silica plug and toluene (20 mL) was added. Methyl(triphenylphosphonanylidene) acetate (3.34 g, 10.0 mmol) was added at 23° C. and the mixture was stirred for 12 h. The solvents were then evaporated, ether was added and the mixture was passed through a silica plug. The mixture was concentrated in vacuo and dried overnight via high vacuum and 585 mg of the above named enoate was obtained as a tan solid.

EXAMPLE 46

3-(2,5-Dibromothiophen-3-yl)propionic Acid Methyl Ester

The enoate of Example 45 was dissolved in THF (6 mL) and purged with argon for 10 min. Wilkinson's catalyst (300 mg) was added and the reaction vessel was evacuated under vacuum and purged with hydrogen (this purge/$H_{2(g)}$ introduction) sequence was repeated 2x. The reaction stirred overnight, the THF was evaporated, hexane was added and the mixture was filtered through a combination pad of celite (lower layer) and silica gel (upper layer). The filter pad was rinsed with $Et_2O$/hex and the filtrate was concentrated to afford 395 mg of the above named ester.

EXAMPLE 47

[4-(2,5-Dibromothiophen-3-yl)-2-oxo-butyl] phosphonic Acid Dimethyl Ester n-BuLi (4.5 mL, 1.6 M in hexane, 7.2 mmol) was added to a solution of dimethyl ethylphosphonate (1.04 g, 8.37 mmol) in THF (30 mL) at −78° C. After 30 min, he ester of Example 46 (1.83 g, 5.58 mmol) in THF (10 mL) was added. The reaction stirred 1 h at −78° C., 1 h at 23° C. and was then quenched with saturated aqueous $NH_4Cl$. The THF was evaporated and the mixture was extracted with $CH_2Cl_2$ (3×). The combined organics were washed with brine, dried ($Na_2SO_4$), filtered and concentrated in vacuo. FCC (silica gel, 50–100% EtOAc/hex) afforded 1.83 g of the above named phosphonate.

EXAMPLE 48

(Z)-7-[(1R,2S,3R,5S)-2-(tert-Butyldimethylsilanyloxymethyl)-3,5-bis-(tetrahydro-pyran-2-yloxy)cyclopentyl]hept-5-en-1-ol The compound of Example 28 is reacted according to the procedure of Example 19 to yield the named compound.

EXAMPLE 49

(Z)-7-[(1R,2S,3R,5S)-2-(tert-Butyldimethylsilanyloxymethyl)-3,5-bis-(tetrahydro-pyran-2-yloxy)cyclopentyl]hept-5-en-1-ol The compound of Example 48 is reacted according to the procedure of Example 20 to yield the named compound.

EXAMPLE 50

(Z)-9-[(1R,2S,3R,5S)-2-(tert-Butyldimethylsilanyloxymethyl)-3,5-bis-(tetrahydro-pyran-2-yloxy)cyclopentyl]-3-hydroxy-2-(tetrahydropyran-2-yloxy)non-7-enoic Acid Methyl Ester LDA (0.38 mL of a 1.5 M solution in cyclohexane, 0.57 mmol) was added to a stirred solution of ester (99 mg, 0.57 mmol) at −78° C. The mixture was stirred for 15 min then aldehyde of example 49 in THF (0.5 mL) was added and the reaction was stirred at −78° C. for 30 min. The reaction was quenched with saturated aqueous $NH_4Cl$ and the THF was evaportated. The aqueous phase was extracted with $CH_2Cl_2$ (3×). The combined organics were washed with brine, dried ($Na_2SO_4$), filtered and concentrated in vacuo. FCC (silica gel 1:5, EtOAc/hex) afforded the desired ester (81 mg).

EXAMPLE 51

(Z)-9-[(1R,2S,3R,5S)-2-(tert-Butyldimethylsilanyloxymethyl)-3,5-bis-(tetrahydro-pyran-2-yloxy)cyclopentyl]-3-oxo-2-(tetrahydropyran-2-yloxy)non-7-enoic Acid Methyl Ester The compound of Example 50 is reacted according to the procedure of Example 42 to yield the above-name compound.

EXAMPLE 52

(Z)-8-[(1R,2S,3R,5S)-2-(tert-Butyldimethylsilanyloxymethyl)-3,5-bis-(tetrahydro-pyran-2-yloxy)cyclopentyl]-1-(tetrahydropyran-2-yloxy)oct-6-en-2-one Ketone of example 51 (60 mg, 0.086 mmol), THF (3 mL), and LiOH (0.3 mL, 1M in $H_2O$, 0.34 mmol;) were combined and refluxed under $N_2$ for 2 h. The THF was evaporated, the aqueous phase was extracted with $CH_2Cl_2$ (2×), and the combined organics were washed with brine and dried ($Na_2SO_4$) filtered and concentrated in vacuo. FCC (silica gel 1:4, EtOAc/hex) afforded the desired ketone (47 mg).

EXAMPLE 53

(Z)-8-[(1R,2S,3R,5S)-2-(tert-Butyldimethylsilanyloxymethyl)-3,5-bis-(tetrahydro-pyran-2-yloxy)cyclopentyl]-1-(tetrahydropyran-2-yloxy)oct-6-en-2-ol The compound of Example 52 is reacted according to the procedure of Example 34 to yield the above named compound.

EXAMPLE 54

Benzoic Acid (Z)-7-[(1R,2S,3R,5S)-2-(tert-butyldimethylsilanyloxymethyl)-3,5-bis-(tetrahydropyran-2-yloxy)cyclopentyl]-1-(tetrahydropyran-2-yloxymethyl)hept-5-enyl Ester The compound of Example 53 is reacted according to the procedure of Example 35 to yield the above named compound.

EXAMPLE 55

Benzoic Acid (Z)-7-[(R,2S,3R,5S)-2-hydroxymethyl-3,5-bis-(tetrahydropyran-2-yloxy)cyclopentyl]-1-(tetrahydropyran-2-yloxymethyl)hept-5-enyl Ester The compound of Example 54 is reacted according to the procedure of Example 36 to yield the above named compound.

EXAMPLE 56

Benzoic Acid (Z)-7-[(1R,2R,3R,5S)-2-formyl-3,5-bis-(tetrahydropyran-2-yloxy)-cyclopentyl]-1-(tetrahydropyran-2-yloxymethylhept-5-enyl Ester The compound of Example 55 is reacted according to the procedure of Example 37 to yield the above named compound.

EXAMPLE 57

Benzoic Acid (Z)-7-[(1R,2R,3R,5S)-2-[(E)-5-(5-bromothiophen-2-yl)-3-oxo-pent-1-enyl]-3,5-bis-(tetrahydropyran-2-yloxy)cyclopentyl]-1-(tetrahydropyran-2-yloxymethyl)hept-5-enyl Ester The compound of Example 56 is reacted according to the procedure of Example 38 to yield the above named compound.

EXAMPLE 58 AND 59

Benzoic Acid (Z)-7-[(1R,2R,3R,5S)-2-[(S)-(E)-5-(5-bromothiophen-2-yl)-3-hydroxypent-1-enyl]-3,5-bis-(tetrahydropyran-2-yloxy)cyclopentyl]-1-(tetrahydro-pyran-2-yloxymethyl)hept-5-enyl Ester Benzoic Acid (Z)-7-[(1R,2R,3R,5S)-2-[(R)-(E)-5-(5-bromothiophen-2-yl)-3-hydroxypent-1-enyl]-3,5-bis-(tetrahydropyran-2-yloxy)cyclopentyl]-1-(tetrahydro-pyran-2-yloxymethyl)hept-5-enyl Ester The compound of Example 57 is reacted according to the procedure of Example 39 to yield the above named compounds.

EXAMPLE 60

Benzoic Acid (Z)-7-[(1R,2R,3R,5S)-2-[(S)-(E)-5-(5-bromothiophen-2-yl)-3-(tetrahydropyran-2-yloxy)pent-1-enyl]-3,5-bis-(tetrahydropyran-2-yloxy)-cyclopentyl]-1-(tetrahydropyran-2-yloxymethyl)hept-5-enyl Ester The compound of Example 58 is reacted according to the procedure of Example 14 to yield the above named compound.

EXAMPLE 61

(Z)-8-[(1R,2R,3R,5S)-2-[(S)-(E)-5-(5-Bromothiophen-2-yl)-3-(tetrahydropyran-5 2-yloxy)pent-1-enyl]-3,5-bis-(tetrahydropyran-2-yloxy)cyclopentyl]-1-(tetrahydro-pyran-2-yloxy)oct-6en-2-ol The compound of Example 60 is reacted according to the procedure of Example 41 to yield the above named compound.

EXAMPLE 62

(Z)-8-[(1R,2R,3R,5S)-2-[(S)-(E)-5-(5-Bromothiophen-2-yl)-3-(tetrahydropyran-2-yloxy)pent-1-enyl]-3,5-bis-(tetrahydropyran-2-yloxy)cyclopentyl]-1-(tetrahydro-pyran-2-yloxy)oct-6-en-2-one The compound of Example 61 is reacted according to the procedure of Example 43 to yield the above named compound.

EXAMPLE 63

(Z)-8-{(1R,2R,3R,5S)-2-[(S)-(E)-5-(5-Bromothiophen-2-yl)-3-hydroxypent-1-enyl]-3,5-dihydroxycyclopentyl}-1-hydroxyoct-6en-2-one The compound of Example 62 is reacted according to the procedure of Example 43 to yield the above named compound.

EXAMPLE 64

(Z)-7-[(1R,2R,3R,5S)-3,5-Dihydroxy-2-((S)-(E)-3-hydroxy-5-phenylpent-1-enyl)-cyclopentyl]hept-5-enoic Acid Methyl Ester

EXAMPLE 65

(Z)-7-[(1R,2R,3R,5S)-2-[(S)-(E)-5-Phenyl-3-(tetrahydropyran-2-yloxy)pent-1-enyl]-3,5-bis-(tetrahydropyran-2-yloxy)cyclopentyl]hept-5-enoic Acid Methyl Ester The compound of Example 64 is reacted according to the procedure of Example 18 to yield the above named compound.

EXAMPLE 66

(Z)-7-[(1R,2R,3R,5S)-2-[(S)-(E)-5-Phenyl-3-(tetrahydropyran-2-yloxy)pent-1-enyl]-3,5-bis-(tetrahydropyran-2-yloxy)cyclopentyl]hept-5-en-1-ol The compound of Example 65 is reacted according to the procedure of Example 19 to yield the above named compound.

EXAMPLE 67

(Z)-7-[(1R,2R,3R,5S)-2-[(S)-(E)-5-Phenyl-3-(tetrahydropyran-2-yloxy)-pent-1-enyl]-3,5-bis-(tetrahydropyran-2-yloxy)cyclopentyl]hept-5-enal The compound of Example 66 is reacted according to the procedure of Example 42 to yield the above named compound.

EXAMPLE 68

(Z)-3-Hydroxy-9-[(1R,2R,3R,5S)-2-[(S)-(E)-5-phenyl-3-(tetrahydropyran-2-yloxy)-pent-1-enyl]-3,5-bis-(tetrahydropyran-2-yloxy)cyclopentyl]-2-(tetrahydropyran-2-yloxy)non-7-enoic Acid Methyl Ester The compound of Example 67 is reacted according to the procedure of Example 50 to yield the above named compound.

EXAMPLE 69

(Z)-3-Oxo-9-[(1R,2R,3R,5S)-2-[(S)-(E)-5-phenyl-3-(tetrahydropyran-2-yloxy)-pent-1-enyl]-3,5-bis-(tetrahydropyran-2-yloxycyclopentyl]-2-(tetrahydropyran-2-yloxy)non-7-enoic Acid Methyl Ester The compound of Example 68 is reacted according to the procedure of Example 42 to yield the above named compound.

EXAMPLE 70

(Z)-8-[(1R,2R,3R,5S)-2-1(S)-(E)-5-Phenyl-3-(tetrahydropyran-2-yloxy)pent-1-enyl]-3,5-bis-(tetrahydropyran-2-yloxy)cyclopentyl]-1-(tetrahydropyran-2-yloxy)-oct-6-en-2-one The compound of Example 69 is reacted according to the procedure of Example 29 to yield the above named compound.

EXAMPLE 71

(Z)-8-[(1R,2R,3R,5S)-3,5-Dihydroxy-2-((S)-(E)-3-hydroxy-5-phenylpent-1-enyl)-cyclopentyl]-1-hydroxyoct-6-en-2-one The compound of Example 70 is reacted according to the procedure of Example 26 to yield the above named compound.

EXAMPLE 72

72(1R,3S,4R,5R)-4-((Z)-7,8-Dihydroxyoct-2-enyl)-5-((S)-(E)-3-hydroxyoct-1-enyl)cyclopentane-1,3-diol The compound of Example 11 is reacted according to the procedure of Example 19 to yield the above named compound.

EXAMPLE 73

(1R,3S,4R,5R)-4-((Z)-6,7-Dihydroxyhept-2-enyl)-5-((S)-(E)-3-hydroxyoct-1-enyl)-cyclopentane-1,3-diol The compound of Example 27 is reacted according to the procedure of Example 19 to yield the above named compound.

EXAMPLE 74

Benzoic acid (Z)-7-{(1R,2R,3R,5S)-2-[(S)-(E)-5-(5-bromothiophen-2-yl)-3-hydroxypent-1-enyl]-3,5-dihydroxycyclopentyl}-1-hydroxymethylhept-5-enyl Ester The compound of Example 58 is reacted according to the procedure of Example 26 to yield the above named compound.

EXAMPLE 75

Benzoic Acid (Z)-7-[(1R,2R,3R,5S)-2-[(S)-(E)-5-(5-bromo-thiophen-2-yl)-3-methoxypent-1-enyl]-3,5-bis-(tetrahydropyran-2-yloxy)cyclopentyl]-1-(tetrahydro-pyran-2-yloxymethyl)hept-5-enyl Ester Sodium hydride (10 mg, 0.26 mmol; 60% dispersion in oil) was added to a solution of alcohol 58 (110 mg, 0.13 mmol) in DMF (10 mL) at 0° C. After 20 min iodomethane (24.3 µL, 0.39 mmol) was added and the reaction was warmed to room temperature. After 4 h, the mixture was poured into saturated aqueous $NH_4Cl$ and the mixture was extracted three times with EtOAc. The combined organics were dried ($Na_2SO_4$) and concentrated. FCC (1:0, 3:1, 2:1; hex/EtOAc) gave 70 mg of product.

EXAMPLE 76

Benzoic Acid (Z)-7-{(1R,2R,3R,5S)-2-[(S)-(E)-5-(5-bromothiophen-2-yl)-3-methoxypent-1-enyl]-3,5-dihydroxycyclopentyl}-1-hydroxymethylhept-5-enyl Ester The compound of Example 75 is reacted according to the procedure of Example 26 to yield the above named compound.

EXAMPLE 77

(Z)-8-[(1R,2R,3R,5S)-2-[(S)-(E)-5-(5-Bromothiophen-2-yl)-3-methoxypent-1-enyl]-3,5-bis-(tetrahydropyran-2-yloxy)cyclopentyl]-1-(tetrahydropyran-2-yloxy)-oct-6-en-2-ol The compound of Example 75 is reacted according to the procedure of Example 41 to yield the above named compound.

EXAMPLE 78

(1S,3R,4R,5R)-4-[(S)-(E)-5-(5-Bromothiophen-2-yl)-3-methoxypent-1-enyl]-5-((Z)-7,8-dihydroxyoct-2-enyl)cyclopentane-1,3-diol The compound of Example 77 is reacted according to the procedure of Example 26 to yield the above named compound.

EXAMPLE 79

(Z)-8-[(1R,2R,3R,5S)-2-[(S)-(E)-5-(5-Bromothiophen-2-yl)-3-methoxypent-1-enyl]-3,5-bis-(tetrahydropyran-2-yloxy)cyclopentyl]-1-(tetrahydropyran-2-yloxy)-oct-6-en-2-one The compound of Example 77 is reacted according to the procedure of Example 42 to yield the above named compound.

EXAMPLE 80

(Z)-8-{(1R,2R,3R,5S)-2-[(S)-(E)-5-(5-Bromothiophen-2-yl)-3-methoxypent-1-enyl]-3,5-dihydroxycyclopentyl}-1-hydroxyoct-6-en-2-one The compound of Example 79 is reacted according to the procedure of Example 26 to yield the above named compound.

EXAMPLE 81

(1S,3R,4R,5R)-4-[(S)-(E)-5-(5-Bromothiophen-2-yl)-3-hydroxypent-1-enyl]-5-((Z)-7,8-dihydroxyoct-2-enyl)cyclopentane-1,3-diol The compound of Example 61 is reacted according to the procedure of Example 26 to yield the above named compound.

EXAMPLE 82

Benzoic Acid (Z)-7-[(1R,2R,3R,5S)-2-[(R)-(E)-5-(5-bromothiophen-2-yl)-3-(tetrahydropyran-2-yloxy)pent-1-enyl]-3,5-bis-(tetrahydropyran-2-yloxy)-cyclopentyl]-1-(tetrahydropyran-2-yloxymethyl)hept-5-enyl Ester The compound of Example 59 is reacted according to the procedure of Example 14 to yield the above named compound.

EXAMPLE 83

(Z)-8-[(1R,2R,3R,5S)-2-[(R)-(E)-5-(5-Bromothiophen-2-yl)-3-(tetrahydropyran-2-yloxy)pent-1-enyl]-3,5-bis-(tetrahydropyran-2-yloxy)cyclopentyl]-1-(tetrahydro-pyran-2-yloxy)oct-6en-2-ol The compound of Example 82 is reacted according to the procedure of Example 41 to yield the above named compound.

EXAMPLE 84

(Z)-8-[(1R,2R,3R,5S)-2-[(R)-(E)-5-(5-Bromothiophen-2-yl)-3-(tetrahydropyran-2-yloxy)pent-1-enyl]-3,5-bis-(tetrahydropyran-2-yloxy)cyclopentyl]-1-(tetrahydro-pyran-2-yloxy)oct-6-en-2-one The compound of Example 83 is reacted according to the procedure of Example 42 to yield the above named compound.

EXAMPLE 85

(Z)-8-{(1R,2R,3R,5S)-2-[(R)-(E)-5-(5-Bromothiophen-2-yl)-3-hydroxypent-1-enyl]-3,5-dihydroxycyclopentyl}-1-hydroxyoct-6-en-2-one The compound of Example 84 is reacted according to the procedure of Example 26 to yield the above named compound.

The compounds of the following examples are prepared by one or more of the process disclosed for Examples 1–85 above.

EXAMPLE 86

Benzoic Acid (Z)-7-{(1R,2R,3R,5S)-2-[(S)-(E)-5-(4-chloro-5-methyl-thiophen-2-yl)-3-hydroxy-pent-1-enyl]-3,5-dihydroxy-cyclopentyl-}-1-hydroxymethyl-hept-5-enyl Ester

EXAMPLE 87

(1S,3R,4R,5R)-4-[(S)-(E)-5-(4-Chloro-5-methyl-thiophen-2-yl)-3-methoxy-pent-1-enyl]-5-((Z)-7,8-dihydroxy-oct-2-enyl)-cyclopentane-1,3-diol

EXAMPLE 88

(1S,3R,4R,5R)-4-[(S)-(E)-5-(4-Chloro-5-methyl-thiophen-2-yl)-3-hydroxy-pent-1-enyl]-5-((Z)-7,8-dihydroxy-oct-2-enyl)-cyclopentane-1,3-diol

EXAMPLE 89

(Z)-8-{(1R,2R,3R,5S)-2-[(S)-(E)-5-(4-Chloro-5-methyl-thiophen-2-yl)-3-hydroxy-pent-1-enyl]-3,5-dihydroxy-cyclopentyl}-1-hydroxy-oct-6-en-2-one

EXAMPLE 90

(Z)-8-{(1R,2R,3R,5S)-2-[(R)-(E)-5-(4-Chloro-5-methyl-thiophen-2-yl)-3-hydroxy-pent-1-enyl]-3,5-dihydroxy-cyclopentyl}-1-hydroxy-oct-6-en-2-one

EXAMPLE 91

Benzoic Acid (Z)-7-{(1R,2R,3R,5S)-3,5-dihydroxy-2-[(S)-(E)-3-hydroxy-5-(5-methyl-thiophen-2-yl)-pent-1-enyl]-cyclopentyl}-1-hydroxymethyl-hept-5-enyl Ester

EXAMPLE 92

(1R,3S,4R,5R)-4-((Z)-7,8-Dihydroxy-oct-2-enyl)-5-[(S)-(E)-3-hydroxy-5-(5-methyl-thiophen-2-yl)-pent-1-enyl]-cyclopentane-1,3-diol

EXAMPLE 93

(Z)-8-{(1R,2R,3R,5S)-3,5-Dihydroxy-2-[(S)-(E)-3-methoxy-5-(5-methyl-thiophen-2-yl)-pent-1-enyl]-cyclopentyl}-1-hydroxy-oct-6-en-2-one

EXAMPLE 94

(Z)-8-{(1R,2R,3R,5S)-3,5-Dihydroxy-2-[(S)-(E)-3-hydroxy-5-(5-methyl-thiophen-2-yl)-pent-1-enyl]-cyclopentyl}-1-hydroxy-oct-6-en-2-one

EXAMPLE 95

(1S,3R,4R,5R)-4-[(S)-(E)-5-(5-Chloro-thiophen-2-yl)-3-methoxy-pent-1-enyl]-5-((Z)-7,8-dihydroxy-oct-2-enyl)-cyclopentane-1,3-diol

EXAMPLE 96

(1S,3R,4R,5R)-4-(S)-(E)-5-(5-Chloro-thiophen-2-yl)-3-hydroxy-pent-1-enyl]-5-((Z)-7,8-dihydroxy-oct-2-enyl)-cyclopentane-1,3-diol

EXAMPLE 97

(1S,3R,4R,5R)-4-[(R)-(E)-5-(5-Chloro-thiophen-2-yl)-3-hydroxy-pent-1-enyl]-5-((Z)-7,8-dihydroxy-oct-2-enyl)-cyclopentane-1,3-diol

EXAMPLE 98

(Z)-8-{(1R,2R,3R,5S)-2-[(S)-(E)-5-(5-Chloro-thiophen-2-yl)-3-methoxy-pent-1-enyl]-3,5-dihydroxy-cyclopentyl}-1-hydroxy-oct-6-en-2-one

EXAMPLE 99

(Z)-8-{(1R,2R,3R,5S)-2-[(S)-(E)-5-(5-Chloro-thiophen-2-yl)-3-hydroxy-pent-1-enyl]-3,5-dihydroxy-cyclopentyl}-1-hydroxy-oct-6-en-2-one

EXAMPLE 100

(Z)-8-{(1R,2R,3R,5S)-2-[(R)-(E)-5-(5-Chloro-thiophen-2-yl)-3-hydroxy-pent-1-enyl]-3,5-dihydroxy-cyclopentyl}-1-hydroxy-oct-6-en-2-one

EXAMPLE 101

Acetic Acid (Z)-8-{(1R,2R,3R,5S)-2-[(S)-(E)-5-(5-chloro-thiophen-2-yl)-3-hydroxy-pent-1-enyl]-3,5-dihydroxy-cyclopentyl}-2-oxo-oct-6-enyl Ester

EXAMPLE 102

Acetic Acid (Z)-8-{(1R,2R,3R,5S)-3-acetoxy-2-[(S)-(E)-5-(5-chloro-thiophen-2-yl)-3-hydroxy-pent-1-enyl]-5-hydroxy-cyclopentyl}-2-oxo-oct-6-enyl Ester Certain of the above compounds were tested for activity in the in vitro assay described below and the results are reported in Table 1 below. Activity was measured in vitro in isolated smooth muscle preparations. FP-activity was measured as contraction of the isolated feline iris sphincter. FP-activity is correlated with lowering intraocular pressure or treating glaucoma, etc.

| Structure | Example | FP |
|---|---|---|
| 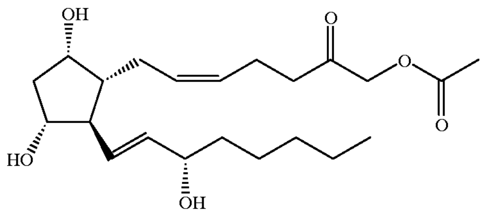 | 26 | NA |
| 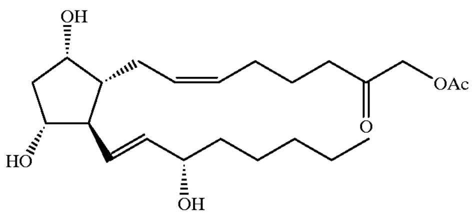 | 10 | 223 |
| 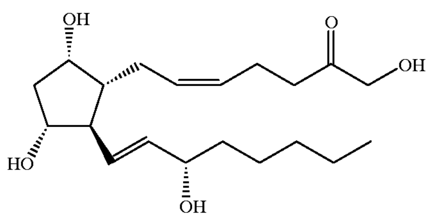 | 27 | 7466 |
| 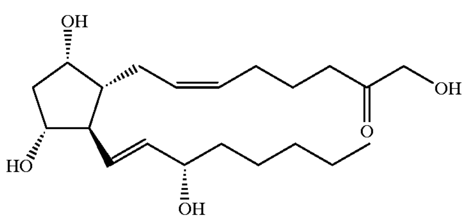 | 11 | 165 |
| 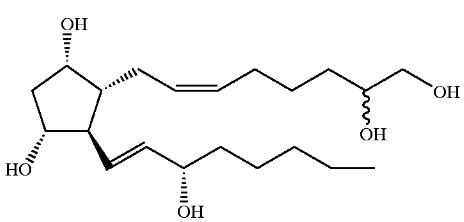 | 72 | 1449 |
| 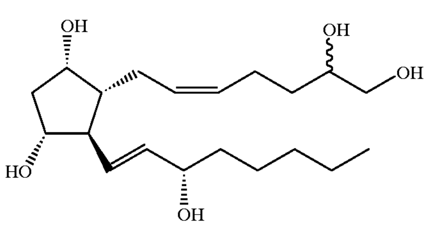 | 73 | NA |

-continued

| Structure | Example | FP |
|---|---|---|
| (structure) | 43 | 54 |
| (structure) | 71 | 10 |
| (structure) | 63 | 4.3 |
| (structure) | 80 | 8.4 |
| (structure) | 74 | 6026 |
| (structure) | 76 | $=10^4$ |

-continued

| Structure | Example | FP |
|---|---|---|
| (structure) | 78 | 1000 |
| (structure) | 81 | 38 |
| (structure) | 85 | 26 |
| (structure) | 86 | 3597 |
| (structure) | 87 | 466 |

-continued

| Structure | Example | FP |
|---|---|---|
| 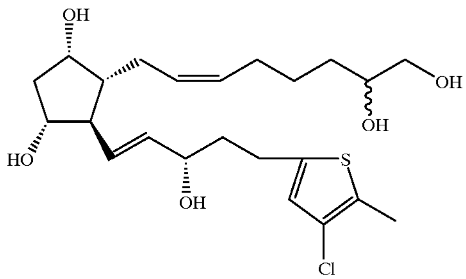 | 88 | 271 |
| 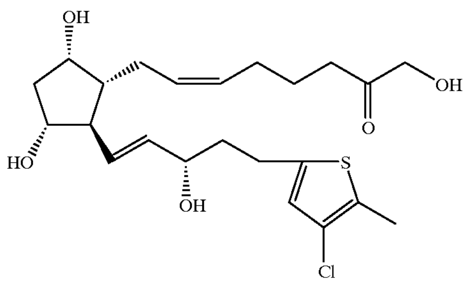 | 89 | 3.6 |
| 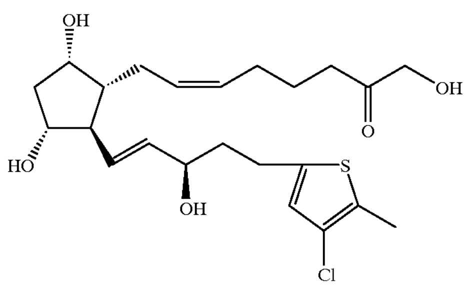 | 90 | 48 |
| 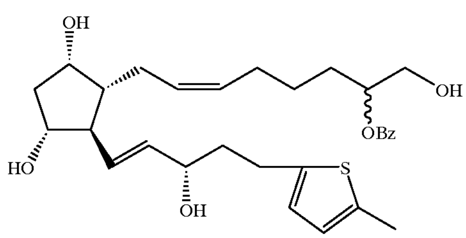 | 91 | 3246 |
| 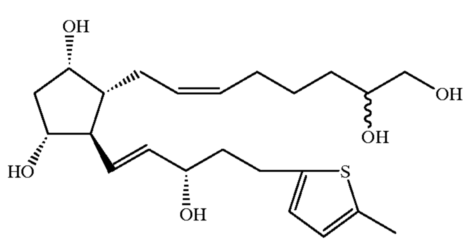 | 92 | 864 |

-continued
| Structure | Example | FP |
|---|---|---|
| 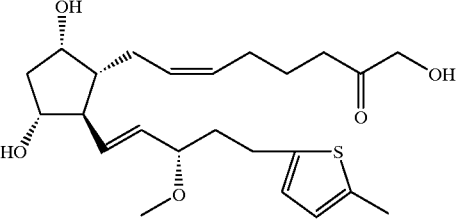 | 93 | 374 |
| 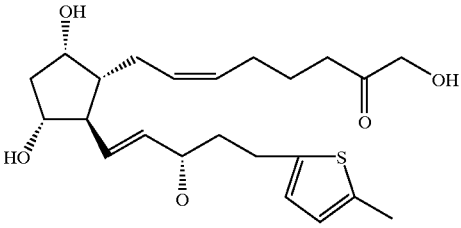 | 94 | 39 |
| 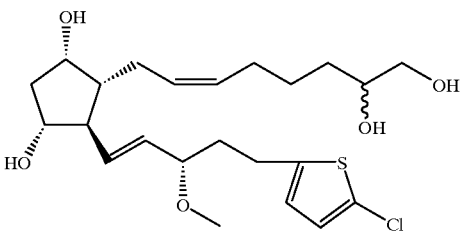 | 95 | 294 |
| 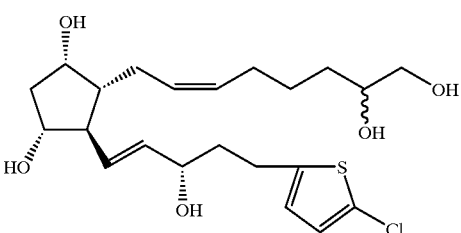 | 96 | 424 |
| 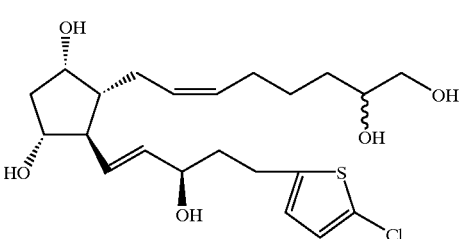 | 97 | 565 |
| 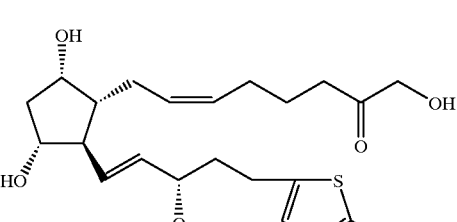 | 98 | 13 |

-continued

| Structure | Example | FP |
|---|---|---|
| 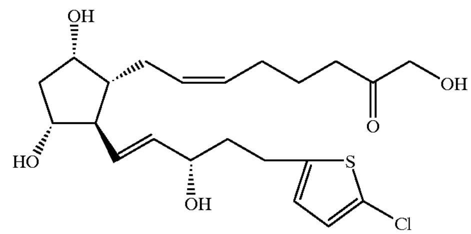 | 99 | 6.7 |
| 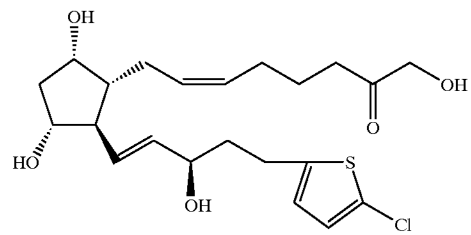 | 100 | 55 |
| 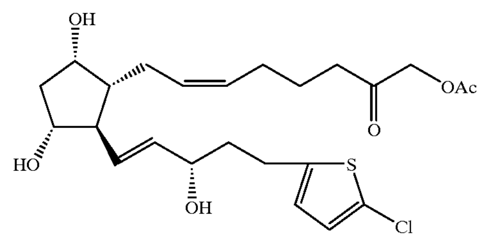 | 101 | |
| 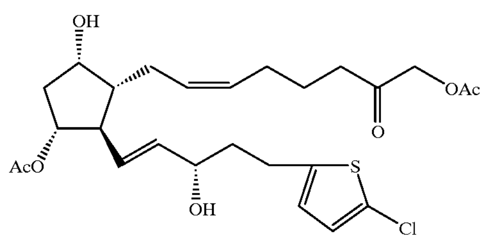 | 102 | |

Other potential therapeutic applications are in osteoporosis, constipation, renal disorders, sexual dysfunction, baldness, diabetes, cancer and in disorder of immune regulation.

Many examples also have pronounced activity at the FP receptor, provisionally termed $FP_{vasc}$ associated with the vascular endothelium in the rabbit jugular vein preparation. Since such agents would be vasodilators they have potential in hypertension and any disease where tissue blood perfusion is compromised. Such indications include, but are not limited to, systemic hypertension, angina, stroke, retinal vascular diseases, claudication, Raynauds disease, diabetes, and pulmonary hypertension.

The effects of the compounds of this invention on intraocular pressure are also provided in the following tables. The compounds were prepared at the said concentrations in a vehicle comprising 0.1% polysorbate 80 and 10 mM TRIS base. Dogs were treated by administering 25 μl to the ocular surface, the contralateral eye received vehicle as a control. Intraocular pressure was measured by applanation pneumatonometry. Dog intraocular pressure was measured immediately before drug administration and at 6 hours thereafter.

Figure 9:
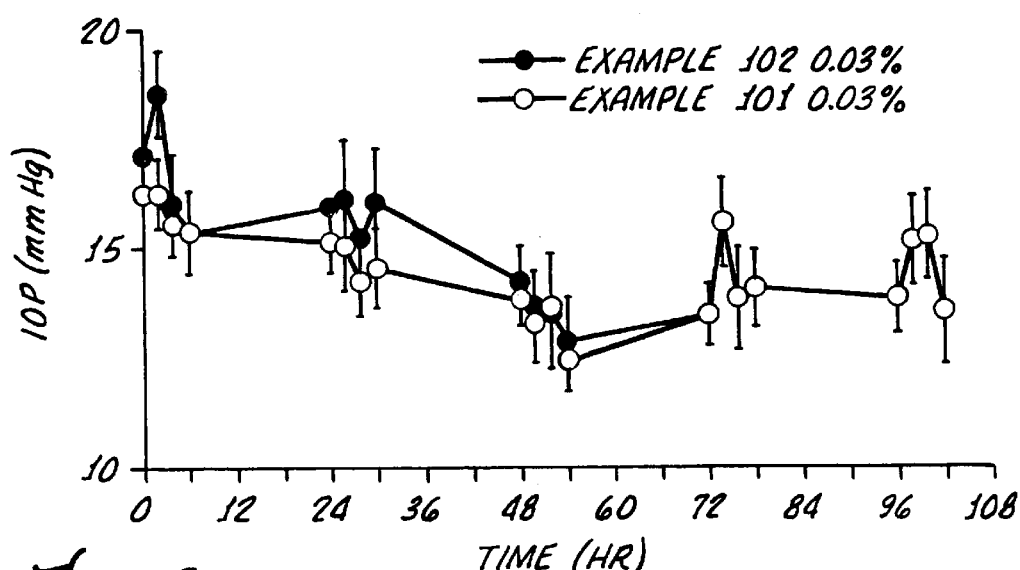
FIG. 9 shows the effect of compounds of Examples 101 and 102 in lowering intraocular pressure.

The compounds of Examples 101 and 102 were examined and showed a pronounced ocular hypotensive effect in dogs. See FIG. 9.

The compounds of the invention may also be useful in the treatment of various pathophysiological diseases including acute myocardial infarction, vascular thrombosis, hypertension, pulmonary hypertension, ischemic heart disease, congestive heart failure, and angina pectoris, in which case the compounds may be administered by any means that effect vasodilation and thereby relieve the symptoms of the disease. For example, administration may be by oral, transdermal, parenteral, subcutaneous, intravenous, intramuscular, intraperitoneal, transdermal, or buccal routes.

The compounds of the invention may be used alone, or in combination with other of the known vasodilator drugs.

The compounds of the invention may be formulated into an ointment containing about 0.10 to 10% of the active ingredient in a suitable base of, for example, white petrolatum, mineral oil and petrolatum and lanolin alcohol. Other suitable bases will be readily apparent to those skilled in the art.

The pharmaceutical preparations of the present invention are manufactured in a manner which is itself known, for example, by means of conventional dissolving or suspending the compounds, which are all either water soluble or suspendable, for administration in the treatment of the other mentioned pathophysiological disorders. The pharmaceutical preparations which can be used orally include push-fit capsules made of gelatin, as well as soft, sealed capsules made of gelatin and a plasticizer such as glycerol or sorbitol. The push-fit capsules can contain the active compounds in liquid form that may be mixed with fillers such as lactose, binders such as starches, and/or lubricants such as talc or magnesium stearate and, optionally, stabilizers. In soft capsules, the active compounds are preferably dissolved or suspended in suitable liquids, such as in buffered salt solution. In addition, stabilizers may be added.

In addition to being provided in a liquid form, for example in gelatin capsule or other suitable vehicle, the pharmaceutical preparations may contain suitable excipients to facilitate the processing of the active compounds into preparations that can be used pharmaceutically. Thus, pharmaceutical preparations for oral use can be obtained by adhering the solution of the active compounds to a solid support, optionally grinding the resulting mixture and processing the mixture of granules, after adding suitable auxiliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch, paste using for example, maize starch, wheat starch, rich starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or algenic acid or a salt thereof, such as sodium alginate. Flow-regulating agents and lubricants may be included, for example, silica, talc, stearic acid or salts thereof, such as magnesium stearate or calcium stearate, and/or polyethylene glycol. Dragee cores are provided with suitable coatings which if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Suitable formulations for intravenous or parenteral administration include aqueous solutions of the active compounds. In addition, suspensions of the active compounds as oily injection suspensions may be administered. Aqueous injection suspensions may contain substances which increase the viscosity of the suspension include, for example, sodium carboxymethyl cellulose, soribitol, and/or dextran. Optionally, the suspension may also contain stabilizers.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. Novel compound represented by the general formula

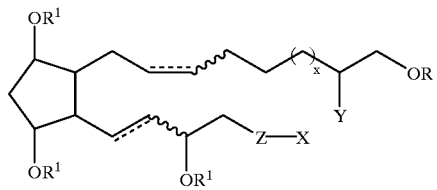

I wherein R is H or $COR^3$;

$R^1$ is H, $R^2$, phenyl, or $COR^3$, wherein $R^2$ is $C_1$–$C_5$ lower alkyl and $R^3$ is $R^2$ or phenyl;

Z is O;

Y is OH or $OCOR^3$;

x is 0 or 1; and

X is $C_1$–$C_5$ n-alkyl or substituted derivatives thereof, wherein the substituents maybe selected from the group consisting of $C_1$–$C_5$ alkyl, halogen, $CF_3$, CN, $NO_2$, $NR^4_2$, $CO_2R^4$ and $OR^4$ wherein $R^4$ is hydrogen or $C_1$–$C_5$ alkyl and dotted lines represent the presence or absence of a double bond and wavy lines represent a cis or trans bond.

2. A compound according to claim 1, represented by the general formula II;

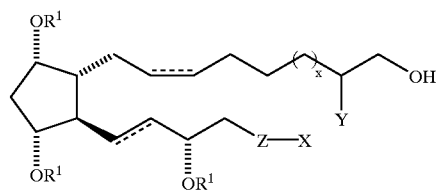

wherein hatched lines indicate the α configuration and a triangle indicates the β configuration.

3. A compound according to claim 2 represented by the general formula III;

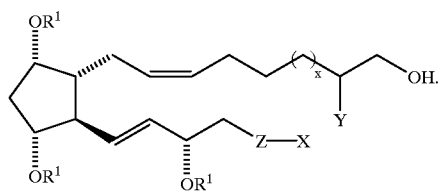

4. The compound of claim 3 wherein Y is OH.
5. The compound of claim 3 wherein x is 0.
6. The compound of claim 3 wherein x is 1.
7. The compound of claim 3 wherein $R^1$ is selected from the group consisting of H and $CH_3$.
8. The compound of claim 1 wherein R is H.

* * * * *

UNITED STATES PATENT AND TRADEMARK OFFICE
CERTIFICATE OF CORRECTION

PATENT NO.    : 6,359,181 B1
DATED         : March 19, 2002
INVENTOR(S)   : Burk et al.

It is certified that error appears in the above-identified patent and that said Letters Patent is hereby corrected as shown below:

Column 6,
Line 2, delete "methoxypent" and insert in place thereof -- hydroxypent --
Line 4, delete "(S)" and insert in place thereof -- (R) --
Line 5, delete "methoxy" and insert in place thereof -- hydroxy --

Column 10,
Line 48, delete "Hydroxy 4" and insert in place thereof -- Hydroxy-4 --
Line 67, delete "pyridinump" and insert in place thereof -- pyridinum p --

Column 11,
Line 26, delete "hex4" and insert in place thereof -- hex-4 --

Column 14,
Line 17, delete "6en" and insert in place thereof -- 6-en --

Column 17,
Line 7, delete "he" and insert in place thereof -- the --
Line 28, delete "5-en-1-ol" and insert in place thereof -- 5-enal --

Column 18,
Line 28, delete "R" and insert in place thereof -- 1R --

Column 19,
Line 15, delete "5"
Lines 17 and 38, delete "6en" and insert in place thereof -- 6-en --

UNITED STATES PATENT AND TRADEMARK OFFICE
CERTIFICATE OF CORRECTION

PATENT NO.    : 6,359,181 B1
DATED         : March 19, 2002
INVENTOR(S)   : Burk et al.

It is certified that error appears in the above-identified patent and that said Letters Patent is hereby corrected as shown below:

Column 22,
Line 25, delete "6en" and insert in place thereof -- 6-en --

Signed and Sealed this

Third Day of September, 2002

Attest:

Attesting Officer

JAMES E. ROGAN
Director of the United States Patent and Trademark Office